United States Patent
Janatpour et al.

(10) Patent No.: US 8,846,005 B2
(45) Date of Patent: Sep. 30, 2014

(54) APCDD1 INHIBITORS FOR TREATING, DIAGNOSING OR DETECTING CANCER

(75) Inventors: Mary J. Janatpour, Emeryville, CA (US); Abdallah Fanidi, Emeryville, CA (US); Shanling Shen, Emeryville, CA (US); Karen Yu, Emeryville, CA (US)

(73) Assignee: Novartis AG, Basel (CH)

( * ) Notice: Subject to any disclaimer, the term of this patent is extended or adjusted under 35 U.S.C. 154(b) by 891 days.

(21) Appl. No.: 12/450,175

(22) PCT Filed: Mar. 14, 2008

(86) PCT No.: PCT/US2008/057026
§ 371 (c)(1),
(2), (4) Date: Apr. 26, 2010

(87) PCT Pub. No.: WO2008/112988
PCT Pub. Date: Sep. 18, 2008

(65) Prior Publication Data
US 2010/0209342 A1    Aug. 19, 2010

Related U.S. Application Data

(60) Provisional application No. 60/894,806, filed on Mar. 14, 2007.

(51) Int. Cl.
*A61K 49/00* (2006.01)
*A61K 51/00* (2006.01)
*C07K 16/00* (2006.01)
*C07K 16/30* (2006.01)
*C07K 14/47* (2006.01)
*C12N 15/113* (2010.01)

(52) U.S. Cl.
CPC ......... *C07K 16/3046* (2013.01); *C12N 2310/14* (2013.01); *C07K 14/4748* (2013.01); *C12N 15/113* (2013.01)
USPC ......................... 424/9.1; 424/1.49; 530/387.1

(58) Field of Classification Search
USPC ................. 424/9.1, 1.49, 133.1, 139.1, 155.1
See application file for complete search history.

(56) References Cited

U.S. PATENT DOCUMENTS

2003/0148410 A1 *    8/2003   Berger et al. ................ 435/7.23

FOREIGN PATENT DOCUMENTS

WO         WO03/104276        12/2003

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Benedict et al (J. Exp. Medicine, 2001, 193(1) 89-99).*
Jiang et al (JBC, 2003, 278(7) 4763-4769).*
Matsushita et al (FEBS Letters, 1999, vol. 443, pp. 348-352).*
Singh et al (Glycobiology, 2001, vol. 11, pp. 587-592).*
Meiko Takahashi et al., "Isolation of a Novel Human Gene, APCDD1, as a Direct Target on the Beta-Catenin/T-Cell Factor 4 Complex with Probable Involvement in Colorectal Carcinogenesis" Cancer Research 62:5651-5656, Oct. 15, 2002.
Birgit Zirn et al., "Target Genes of the WNT/Beta-Catenin Pathway in Wilms Tumors" Genes, Chromosomes and Cancer 45:565-574, 2006.
Tomi Jukkola et al., "Drapc1 Expression During Mouse Embryonic Development" Gene Expression Patterns 4 (6):755-762, Oct. 1, 2004.

* cited by examiner

*Primary Examiner* — Mark Halvorson
*Assistant Examiner* — Yan Xiao
(74) *Attorney, Agent, or Firm* — David A. Carpenter

(57) ABSTRACT

The invention provides, inter alia, methods for methods for treating cancer, compositions for treating cancer, and methods and compositions for diagnosing and/or detecting cancer. In particular, the present invention provides compositions and methods for treating, diagnosing and detecting cancers associated with APCDD1 overexpression.

4 Claims, 14 Drawing Sheets

Expression of APCDD1 protein in human cancer cells

APCDD1 is glycosylated

APCDD1 upregulates cyclin D1 protein in Rat-1 cells

Characterization of APCDD1 Rat Monoclonal Antibody #4 by Western Blot and FACS

APCDD1 protein sequence (SEQ ID NO:2)

MSWPRRLLLRYLFPALLLHGLGEGS ALLHPDSRSHPRSLEKSAWRAFKESQCHH
MLKHLHNGARITVQMPPTIEGHWVSTGCEVRSGPEFITRSYRFYHNNTFKAYQF
YYGSNRCTNPTYTLIIRGKIRLRQASWIIRGGTEADYQLHNVQVICHTEAVAEK
LGQQVNRTCPGFLADGGPWVQDVAYDLWREENGCECTKAVNFAMHELQLIRVEK
QYLHHNLDHLVEELFLGDIHTDATQRMFYRPSSYQPPLQNAKNHDHACIACRII
YRSDEHHPPILPPKADLTIGLHGEWVSQRCEVRPEVLFLTRHFIFHDNNNTWEG
HYYHYSDPVCKHPTFSIYARGRYSRGVLSSRVMGGTEFVFKVNHMKVTPMDAAT
ASLLNVFNGNECGAEGSWQVGIQQDVTHTNGCVALGIKLPHTEYEIFKMEQDAR
GRYLLFNGQRPSDGSSPDRPEKRATSYQMPLVQCASSSPRAEDLAEDSGSSLYG
RAPGRHTWSLLAALACLVPLLHWNIRR

TM - bold
Cytop - underlined
Signal - *underlined and italics*
ECD - *italics*

SEQUENCE LISTING

```
<160> NUMBER OF SEQ ID NOS: 25

<210> SEQ ID NO 1
<211> LENGTH: 2572
<212> TYPE: DNA
<213> ORGANISM: Homo sapiens

<400> SEQUENCE: 1
gaaatatgaa gagacgctgc agctgcggtg gcggtggcgg ccactgcagc tcagagcggc      60
gcacgcggcg gccggggcgg gacgcggggc cgggcgcgga gaagtcgggg cgggcggcag     120
agaggccggg acgcggaccg ggccggggcg cccacagccg cccgacggcg cccagagagc     180
gcgcgccccg cagccccgcg cctagcccgc cgggcatggg gcgcgcggca gccgcctgaa     240
```

```
gccccggcct ggcccggccg cacccggccg gaggggaggg cagagcgcgc gcccagttgc      300
ccgggcacca aatcggagcg cggcgtgcgg gagggcccag agcaggactg gaaatgtcct      360
ggccgcgccg cctcctgctc agatacctgt tcccggccct cctgcttcac gggctgggag      420
agggttctgc cctccttcat ccagacagca ggtctcatcc taggtcctta gagaaaagtg      480
cctggagggc ttttaaggag tcacagtgcc atcacatgct caaacatctc cacaatggtg      540
caaggatcac agtgcagatg ccacctacaa tcgaggggcca ctgggtctcc acaggctgtg      600
aagtaaggtc aggcccagag ttcatcacaa ggtcctacag attctaccac aataacacct      660
tcaaggccta ccaattttat tatggcagca accggtgcac aaatcccact tatactctca      720
tcatccgggg caagatccgc ctccgccagg cctcctggat catccgaggg ggcacggaag      780
ccgactacca gctgcacaac gtccaggtga tctgccacac agaggcggtg gccgagaagc      840
tcggccagca ggtgaaccgc acatgcccgg gcttcctcgc agacgggggt ccctgggtgc      900
aggacgtggc ctatgacctc tggcgagagg agaacggctg tgagtgcacc aaggccgtga      960
actttgccat gcatgaactt cagctcatcc gggtggagaa gcagtacctt caccacaacc     1020
tcgaccacct ggtcgaggag ctcttccttg gtgacattca cactgatgcc acccagagga     1080
tgttctaccg gccctccagt taccagcccc ctctgcagaa tgccaagaac cacgaccatg     1140
cctgcatcgc ctgtcggatc atctatcggt cagacgagca ccaccctccc atcctgcccc     1200
caaaggcaga cctgaccatc ggcctgcacg gggagtgggt gagccagcgc tgtgaggtgc     1260
gccccgaagt cctcttcctc acccgccact tcatcttcca tgacaacaac aacacctggg     1320
agggccacta ctaccactac tcagacccgg tgtgcaagca ccccaccttc tccatctacg     1380 cccgggggccg ctacagccgc ggcgtcctct cgtccagggt catgggaggc accgagttcg     1440
tgttcaaagt gaatcacatg aaggtcaccc ccatggatgc ggccacagcc tcactgctca     1500
acgtcttcaa cgggaatgag tgcggggccg agggctcctg gcaggtgggc atccagcagg     1560
atgtgaccca caccaatggc tgcgtggccc tgggcatcaa actacctcac acggagtacg     1620
agatcttcaa aatggaacag gatgcccggg ggcgctatct gctgttcaac ggtcagaggc     1680
ccagcgacgg gtccagccca gacaggccag agaagagagc cacgtcctac cagatgccct     1740
tggtccagtg tgcctcctct tcgccgaggg cagaggacct cgcagaagac agtggaagca     1800
gcctgtatgg ccgggcccct ggggaggcaca cctggtccct gctgctggct gcacttgcct     1860
gccttgtccc tctgctgcat tggaacatcc gcagatagaa gttttagaaa gttctatttt     1920
ttccaaacca ggattcctta ctattgacag atttgcttta ccaaaagaaa agacatttat     1980
tcttttgatg cacttgaatg ccagagaact gtccttcttt ttctcctctc cctccctccc     2040 agccctgag tcatgaacag caaggagtgt ttgaagtttc tgctttgaac tccgtccagc     2100
ctgatccctg gcctgagcaa cttcacaaca gtaattgcac tttaagacag cctagagttc     2160
tggacgagcg tgtttggtag cagggatgaa agctagggcc tcttatttt ttctcttaat     2220 tattattata tttctgagtt aaacttagaa gaaacaacta tcaagctaca acttttcctg     2280 ccatttcct gtggttgcag cctgtcttcc tttgaaattg ttttactctc tgagttttat     2340
atgctggaat ccaatgcaga gttggtttgg gactgtgatc aagacacctt ttattaataa     2400
agaagagaca caggtgtaga tatgtatata caaaaagatg tacggtctgg ccaaaccacc     2460
ttcccagcct ttatgcaaaa aaaggggaga atcaaagctt tcatttcaga aatgttgcgt     2520
ggaaaagtat ctgtaattaa agtttcgaag taatttaaaa aaaaaaaaaa aa              2572
```

```
<210> SEQ ID NO 2
<211> LENGTH: 514
<212> TYPE: PRT
<213> ORGANISM: Homo sapiens

<400> SEQUENCE: 2

Met Ser Trp Pro Arg Leu Leu Arg Tyr Leu Phe Pro Ala Leu
  1               5                  10                  15

Leu Leu His Gly Leu Gly Glu Gly Ser Ala Leu Leu His Pro Asp Ser
            20                  25                  30

Arg Ser His Pro Arg Ser Leu Glu Lys Ser Ala Trp Arg Ala Phe Lys
        35                  40                  45

Glu Ser Gln Cys His His Met Leu Lys His Leu His Asn Gly Ala Arg
    50                  55                  60

Ile Thr Val Gln Met Pro Pro Thr Ile Glu Gly His Trp Val Ser Thr
65                  70                  75                  80

Gly Cys Glu Val Arg Ser Gly Pro Glu Phe Ile Thr Arg Ser Tyr Arg
                85                  90                  95

Phe Tyr His Asn Asn Thr Phe Lys Ala Tyr Gln Phe Tyr Tyr Gly Ser
                100                 105                 110

Asn Arg Cys Thr Asn Pro Thr Tyr Thr Leu Ile Ile Arg Gly Lys Ile
            115                 120                 125

Arg Leu Arg Gln Ala Ser Trp Ile Ile Arg Gly Thr Glu Ala Asp
        130                 135                 140

Tyr Gln Leu His Asn Val Gln Val Ile Cys His Thr Glu Ala Val Ala
145                 150                 155                 160

Glu Lys Leu Gly Gln Gln Val Asn Arg Thr Cys Pro Gly Phe Leu Ala
                165                 170                 175

Asp Gly Gly Pro Trp Val Gln Asp Val Ala Tyr Asp Leu Trp Arg Glu
            180                 185                 190

Glu Asn Gly Cys Glu Cys Thr Lys Ala Val Asn Phe Ala Met His Glu
        195                 200                 205

Leu Gln Leu Ile Arg Val Glu Lys Gln Tyr Leu His His Asn Leu Asp
    210                 215                 220

His Leu Val Glu Glu Leu Phe Leu Gly Asp Ile His Thr Asp Ala Thr
225                 230                 235                 240

Gln Arg Met Phe Tyr Arg Pro Ser Ser Tyr Gln Pro Pro Leu Gln Asn
                245                 250                 255

Ala Lys Asn His Asp His Ala Cys Ile Ala Cys Arg Ile Ile Tyr Arg
            260                 265                 270

Ser Asp Glu His His Pro Pro Ile Leu Pro Pro Lys Ala Asp Leu Thr
        275                 280                 285

Ile Gly Leu His Gly Glu Trp Val Ser Gln Arg Cys Glu Val Arg Pro
    290                 295                 300

Glu Val Leu Phe Leu Thr Arg His Phe Ile Phe His Asp Asn Asn
305                 310                 315                 320

Thr Trp Glu Gly His Tyr Tyr His Tyr Ser Asp Pro Val Cys Lys His
                325                 330                 335

Pro Thr Phe Ser Ile Tyr Ala Arg Gly Arg Tyr Ser Arg Gly Val Leu
            340                 345                 350

Ser Ser Arg Val Met Gly Gly Thr Glu Phe Val Phe Lys Val Asn His
        355                 360                 365

Met Lys Val Thr Pro Met Asp Ala Ala Thr Ala Ser Leu Leu Asn Val
    370                 375                 380
```

```
Phe Asn Gly Asn Glu Cys Gly Ala Glu Gly Ser Trp Gln Val Gly Ile
385                 390                 395                 400

Gln Gln Asp Val Thr His Thr Asn Gly Cys Val Ala Leu Gly Ile Lys
                405                 410                 415

Leu Pro His Thr Glu Tyr Glu Ile Phe Lys Met Glu Gln Asp Ala Arg
            420                 425                 430

Gly Arg Tyr Leu Leu Phe Asn Gly Gln Arg Pro Ser Asp Gly Ser Ser
        435                 440                 445

Pro Asp Arg Pro Glu Lys Arg Ala Thr Ser Tyr Gln Met Pro Leu Val
    450                 455                 460

Gln Cys Ala Ser Ser Pro Arg Ala Glu Asp Leu Ala Glu Asp Ser
465                 470                 475                 480

Gly Ser Ser Leu Tyr Gly Arg Ala Pro Gly Arg His Thr Trp Ser Leu
                485                 490                 495

Leu Leu Ala Ala Leu Ala Cys Leu Val Pro Leu Leu His Trp Asn Ile
            500                 505                 510

Arg Arg

<210> SEQ ID NO 3
<211> LENGTH: 468
<212> TYPE: PRT
<213> ORGANISM: Homo sapiens

<400> SEQUENCE: 3

Ala Leu Leu His Pro Asp Ser Arg Ser His Pro Arg Ser Leu Glu Lys
1               5                   10                  15

Ser Ala Trp Arg Ala Phe Lys Glu Ser Gln Cys His His Met Leu Lys
            20                  25                  30

His Leu His Asn Gly Ala Arg Ile Thr Val Gln Met Pro Pro Thr Ile
        35                  40                  45

Glu Gly His Trp Val Ser Thr Gly Cys Glu Val Arg Ser Gly Pro Glu
    50                  55                  60

Phe Ile Thr Arg Ser Tyr Arg Phe Tyr His Asn Asn Thr Phe Lys Ala
65                  70                  75                  80

Tyr Gln Phe Tyr Tyr Gly Ser Asn Arg Cys Thr Asn Pro Thr Tyr Thr
                85                  90                  95

Leu Ile Ile Arg Gly Lys Ile Arg Leu Arg Gln Ala Ser Trp Ile Ile
            100                 105                 110

Arg Gly Gly Thr Glu Ala Asp Tyr Gln Leu His Asn Val Gln Val Ile
        115                 120                 125

Cys His Thr Glu Ala Val Ala Glu Lys Leu Gly Gln Gln Val Asn Arg
    130                 135                 140

Thr Cys Pro Gly Phe Leu Ala Asp Gly Gly Pro Trp Val Gln Asp Val
145                 150                 155                 160

Ala Tyr Asp Leu Trp Arg Glu Glu Asn Gly Cys Glu Cys Thr Lys Ala
                165                 170                 175

Val Asn Phe Ala Met His Glu Leu Gln Leu Ile Arg Val Glu Lys Gln
            180                 185                 190

Tyr Leu His His Asn Leu Asp His Leu Val Glu Glu Leu Phe Leu Gly
        195                 200                 205

Asp Ile His Thr Asp Ala Thr Gln Arg Met Phe Tyr Arg Pro Ser Ser
    210                 215                 220

Tyr Gln Pro Pro Leu Gln Asn Ala Lys Asn His Asp His Ala Cys Ile
225                 230                 235                 240
```

Ala Cys Arg Ile Ile Tyr Arg Ser Asp Glu His His Pro Pro Ile Leu
              245                 250                 255

Pro Pro Lys Ala Asp Leu Thr Ile Gly Leu His Gly Glu Trp Val Ser
            260                 265                 270

Gln Arg Cys Glu Val Arg Pro Glu Val Leu Phe Leu Thr Arg His Phe
        275                 280                 285

Ile Phe His Asp Asn Asn Thr Trp Glu Gly His Tyr Tyr His Tyr
    290                 295                 300

Ser Asp Pro Val Cys Lys His Pro Thr Phe Ser Ile Tyr Ala Arg Gly
305                 310                 315                 320

Arg Tyr Ser Arg Gly Val Leu Ser Arg Val Met Gly Gly Thr Glu
            325                 330                 335

Phe Val Phe Lys Val Asn His Met Lys Val Thr Pro Met Asp Ala Ala
            340                 345                 350

Thr Ala Ser Leu Leu Asn Val Phe Asn Gly Asn Glu Cys Gly Ala Glu
            355                 360                 365

Gly Ser Trp Gln Val Gly Ile Gln Gln Asp Val Thr His Thr Asn Gly
        370                 375                 380

Cys Val Ala Leu Gly Ile Lys Leu Pro His Thr Glu Tyr Glu Ile Phe
385                 390                 395                 400

Lys Met Glu Gln Asp Ala Arg Gly Arg Tyr Leu Leu Phe Asn Gly Gln
            405                 410                 415

Arg Pro Ser Asp Gly Ser Ser Pro Asp Arg Pro Glu Lys Arg Ala Thr
            420                 425                 430

Ser Tyr Gln Met Pro Leu Val Gln Cys Ala Ser Ser Pro Arg Ala
            435                 440                 445

Glu Asp Leu Ala Glu Asp Ser Gly Ser Ser Leu Tyr Gly Arg Ala Pro
    450                 455                 460

Gly Arg His Thr
465

<210> SEQ ID NO 4
<211> LENGTH: 25
<212> TYPE: PRT
<213> ORGANISM: Homo sapiens

<400> SEQUENCE: 4

Met Ser Trp Pro Arg Leu Leu Leu Arg Tyr Leu Phe Pro Ala Leu
  1               5                  10                  15

Leu Leu His Gly Leu Gly Glu Gly Ser
            20                  25

<210> SEQ ID NO 5
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 5
gcucaaacau cuccacaauu u                                      21

<210> SEQ ID NO 6
<211> LENGTH: 21
<212> TYPE: RNA
<213> ORGANISM: Artificial Sequence
<220> FEATURE:
<223> OTHER INFORMATION: Synthetically generated siRNA -continued

```
<400> SEQUENCE: 6 auguggaga uguuugaccu u                                                    21

<210> SEQ ID NO 7
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 7
cuucaaggcc uaccauuuu u                                                    21

<210> SEQ ID NO 8
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 8
aaauugguag gccuugaagu u                                                   21

<210> SEQ ID NO 9
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 9
caaacuaccu cacacggagu u                                                   21

<210> SEQ ID NO 10
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 10
cuccguguga gguaguuugu u                                                   21

<210> SEQ ID NO 11
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 11
gcccagaguu caucacaagu u                                                   21

<210> SEQ ID NO 12
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 12
cuugugauga acucugggcu u                                                   21

<210> SEQ ID NO 13
```

```
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 13
ggucucaucc uagguccuut t                                             21

<210> SEQ ID NO 14
<211> LENGTH: 22
<212> TYPE: DNA
<213> ORGANISM: Artificial Sequence
<220> FEATURE:
<223> OTHER INFORMATION: Synthetically generated siRNA

<400> SEQUENCE: 14
aaggaccuag gaugagaacc tg                                            22

<210> SEQ ID NO 15
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 15
gggcuuuuaa ggagucacat t                                             21

<210> SEQ ID NO 16
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 16
ugugacuccu uaaaagccct c                                             21

<210> SEQ ID NO 17
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 17
gguguagaua uguauauact t                                             21

<210> SEQ ID NO 18
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 18
guauauacau aucuacacct g                                             21

<210> SEQ ID NO 19
<211> LENGTH: 25
<212> TYPE: RNA
<213> ORGANISM: Artificial Sequence
<220> FEATURE:
<223> OTHER INFORMATION: Synthetically generated siRNA

<400> SEQUENCE: 19
```

```
ucacuuugaa cacgaacucg gugcc                                               25

<210> SEQ ID NO 20
<211> LENGTH: 25
<212> TYPE: RNA
<213> ORGANISM: Artificial Sequence
<220> FEATURE:
<223> OTHER INFORMATION: Synthetically generated siRNA

<400> SEQUENCE: 20
uuacuucaca gccuguggag accca                                               25

<210> SEQ ID NO 21
<211> LENGTH: 25
<212> TYPE: RNA
<213> ORGANISM: Artificial Sequence
<220> FEATURE:
<223> OTHER INFORMATION: Synthetically generated siRNA

<400> SEQUENCE: 21
uaagugggau uugugcaccg guugc                                               25

<210> SEQ ID NO 22
<211> LENGTH: 16
<212> TYPE: PRT
<213> ORGANISM: Homo sapiens

<400> SEQUENCE: 22

Pro Ser Ser Tyr Gln Pro Pro Leu Gln Asn Ala Lys Asn His Asp His
1               5                   10                  15

<210> SEQ ID NO 23
<211> LENGTH: 20
<212> TYPE: PRT
<213> ORGANISM: Homo sapiens

<400> SEQUENCE: 23

Gln Arg Pro Ser Asp Gly Ser Ser Pro Asp Arg Pro Glu Lys Arg Ala
1               5                   10                  15

Thr Ser Tyr Gln
            20

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
gtcgaggagc tcttccttgg tgacatt                                             27

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
tggtgctcgt ctgaccgata gatgat                                              26
```

APCDD1 INHIBITORS FOR TREATING, DIAGNOSING OR DETECTING CANCER

This application claims priority to U.S. Provisional Application No. 60/894,806 filed Mar. 14, 2007.

FIELD OF THE INVENTION

The present invention relates generally to the field of oncology. More particularly, the invention relates to methods for treating cancer, compositions for treating cancer, and methods and compositions for diagnosing and/or detecting cancer.

BACKGROUND OF THE INVENTION

Cancer is the second leading cause of death in the United States. Although "cancer" is used to describe many different types of cancer, i.e., breast, prostate, lung, colon, pancreas, each type of cancer differs both at the phenotypic level and the genetic level. The unregulated growth characteristic of cancer occurs when the expression of one or more genes becomes dysregulated due to mutations, and cell growth can no longer be controlled.

Genes are often classified in two classes, oncogenes and tumor suppressor genes. Oncogenes are genes whose normal function is to promote cell growth, but only under specific conditions. When an oncogene gains a mutation and then loses that control, it promotes growth under all conditions. However, it has been found that for cancer to be truly successful the cancer must also acquire mutations in tumor suppressor genes. The normal function of tumor suppressor genes is to stop cellular growth. Examples of tumor suppressors include p53, p16, p21, and APC, all of which, when acting normally, stop a cell from dividing and growing uncontrollably. When a tumor suppressor is mutated or lost, that brake on cellular growth is also lost, allowing cells to now grow without restraints.

APCDD1 (also known as B7323, B7323N, DRAPC1 and FP7019) is a polypeptide whose expression is downregulated by the tumor suppressor gene, adenopolyposis coli (APC) (Takahashi et al., Cancer Research 62: 5651-5656, 2002). APCDD1 appears to be up-regulated in colon cancer. Overexpression of APCDD1 in a colon cancer cell line has been shown to stimulate cell growth in vitro and to moderately increase tumor growth in vivo.

To date, however, the role of APCDD1 in cancer and other diseases and disorders has not been fully elucidated. Accordingly there is a need to identify compositions and methods that modulate APCDD1. The present invention is directed to these, as well as other, important needs.

SUMMARY OF THE INVENTION

The present invention provides methods and compositions useful in detection of cancerous cells, identification of agents that modulate the phenotype of cancerous cells, and identification of therapeutic targets for therapy of cancerous cells.

Accordingly, in some aspects the invention provides compositions comprising an APCCD1 modulator and one or more pharmaceutically acceptable carriers, wherein the APCCD1 modulator is an isolated double-stranded RNA (dsRNA); an isolated oligonucleotide comprising at least 10 consecutive nucleotides of a sequence selected from the group consisting of SEQ ID NOs:1, 5-21, 24 and 25; an antibody that binds an epitope in an extracellular domain (ECD) of APCCD1; a small molecule; a mimetic; a soluble receptor, or a decoy.

In some aspects the invention provides purified antibodies that specifically bind to an epitope in the extracellular domain of APCCD1. In some aspects the invention provides isolated cells, hybridomas and non-human transgenic animals that produce such antibodies.

In some aspects the invention provides purified antibodies that specifically bind to one or more epitopes of an APCDD1 polypeptide. In some aspects the epitope comprises a sequence selected from the group consisting of SEQ ID NOs: 3, 4, 22 and 23.

In some aspects the invention provides isolated epitope-bearing fragments of the polypeptide of SEQ ID NO:2, the fragment comprising one or more epitopes selected from the group consisting of SEQ ID NOs: 3, 4, 22 and 23. In some aspects the invention provides polynucleotides encoding such isolated epitope-bearing fragments. In some aspects, the invention provides APCDD1 antibodies obtained through immunization of a subject with such epitope-bearing fragments.

In some aspects the invention provides isolated dsRNA molecules comprising a first strand of nucleotides comprising at least 19 consecutive nucleotides of a sequence set forth in SEQ ID NOs: 1, 5-21, 24 and 25, and a second strand of nucleotides comprising a sequence substantially complementary to the first strand, wherein the dsRNA molecule is less than 2534 nucleotides long.

In some aspects the invention provides isolated nucleic acids comprising at least 10 consecutive nucleotides of a sequence set forth in SEQ ID NOs: 1, 5-21, 24 and 25.

In some aspects the invention provides methods of treating cancer or a cancer symptom in a patient in need thereof comprising administering to the patient a therapeutically effective amount of an APCDD1 inhibitor.

In some aspects the invention provides methods of modulating an APCDD1 activity in a patient, the method comprising administering to the patient an amount of an APCDD1 inhibitor effective to modulate the APCDD1 activity.

In some aspects the invention provides methods of identifying a patient susceptible to APCDD1 therapy comprising (a) detecting the presence or absence of evidence of APCDD1 expression in a sample of the patient, wherein the presence of evidence of APCDD1 expression in the sample is indicative of a patient who is a candidate for APCDD1 therapy and the absence of evidence of APCDD1 expression in the sample is indicative of a patient who is not a candidate for APCDD1 therapy; (b) administering a therapeutically effective amount of an APCDD1 inhibitor to the patient if the patient is a candidate for APCDD1 therapy; and (c) administering a traditional cancer therapeutic to the patient if the patient is not a candidate for APCDD1 therapy.

In some aspects the invention provides methods of inhibiting growth of cancer cells comprising contacting the cancer cells with an amount of an APCDD1 inhibitor effective to inhibit growth of the cells by at least 20% as compared to a control.

In some aspects the invention provides methods of inhibiting a cancer cell phenotype in a patient in need thereof the method comprising administering to the patient a therapeutically effective amount of an APCDD1 inhibitor.

In some aspects the invention provides methods for detecting a tumor in a patient comprising administering to the patient a composition comprising an APCDD1 inhibitor linked to an imaging agent and detecting the localization of the imaging agent in the patient.

In some aspects the invention provides methods of expressing an APCDD1 antibody in a cell wherein the APCDD1 antibody specifically binds to an epitope comprising a sequence selected from the group consisting of SEQ ID NOS: 3, 4, 22 and 23, the method comprising expressing a nucleic acid encoding the APCDD1 antibody in the cell.

In some aspects the invention provides methods of identifying a cancer inhibitor, the cancer characterized by overexpression of APCDD1 compared to a control, the method comprising contacting a cell expressing APCDD1 with a candidate compound and determining whether an APCDD1 activity is modulated, wherein modulation of the APCDD1 activity is indicative of a cancer inhibitor.

In some aspects the invention provides methods of identifying a cancer inhibitor, the cancer characterized by overexpression of APCDD1 compared to a control, the method comprising contacting a cell expressing APCDD1 with a candidate compound and an APCDD1 ligand, and determining whether an activity of a downstream marker of APCDD1 is modulated, wherein modulation of the downstream marker is indicative of a cancer inhibitor.

In some aspects the invention provides methods for determining the susceptibility of a patient to an APCDD1 inhibitor comprising detecting evidence of differential expression of APCDD1 in a patient's cancer sample, wherein evidence of differential expression of APCDD1 is indicative of the patient's susceptibility to the APCDD1 inhibitor.

In some aspects the invention provides methods of purifying APCDD1 protein from a sample comprising (a) providing an affinity matrix comprising an antibody of the invention bound to a solid support; (b) contacting the sample with the affinity matrix to form an affinity matrix-APCDD1 protein complex; (c) separating the affinity matrix-APCDD1 protein complex from the remainder of the sample; and (d) releasing APCDD1 protein from the affinity matrix.

In some aspects the invention provides methods of delivering a cytotoxic agent or a diagnostic agent to one or more cells that express APCDD1, the method comprising: (a) providing the cytotoxic agent or the diagnostic agent conjugated to an APCDD1 antibody or fragment; and (b) exposing the cell to the antibody-agent or fragment-agent conjugate.

In some aspects the invention provides methods for determining the effectiveness of a candidate APCDD1 inhibitor comprising contacting APCDD1-expressing cells with the candidate APCDD1 inhibitor and determining whether a level or activity of a downstream APCDD1 marker is decreased, wherein a decrease in the level or activity of the downstream marker indicates that the candidate APCDD1 inhibitor is an effective anti-cancer medication.

In some aspects the invention provides methods for determining the effectiveness of a candidate APCDD1 inhibitor comprising contacting APCDD1-expressing cells with the candidate APCDD1 inhibitor and determining whether cyclin D1 activity is increased, wherein an increase in cyclin D1 activity indicates that the candidate APCDD1 inhibitor is an effective anti-cancer medication.

In some aspects the invention provides methods of determining whether a cancer is an APCDD1-related cancer comprising comparing APCDD1 expression in cancer and control cells, wherein upregulated APCDD1 expression in the cancer cells as compared to the control cells indicates that the cancer is an APCDD1 related cancer.

In some aspects the invention provides methods of determining whether a cancer is an APCDD1-related cancer comprising contacting a cancer sample and a control sample with an APCDD1 inhibitor, and comparing a level or activity of an APCDD1 downstream marker in the cancer sample and in the control sample, wherein decreased level or activity of the APCDD1 downstream marker in the cancer sample compared to the control sample indicates that the cancer is an APCDD1 related cancer.

In some aspects the invention provides methods of determining whether a cancer is an APCDD1-related cancer comprising contacting a cancer sample and a control sample with an APCDD1 inhibitor, and comparing cyclin D1 activity in the cancer sample and in the control sample, wherein increased cyclin D1 activity in the cancer sample compared to the control sample indicates that the cancer is an APCDD1 related cancer.

In some aspects the invention provides methods of treating a cancer patient comprising determining whether a cancer is an APCDD1-related cancer according to the invention, and administering to the patient a composition of the invention if the patient has an APCDD1-related cancer, and administering to the patient a traditional cancer therapeutic if the patient does not have an APCDD1-related cancer.

In some aspects the invention provides methods of treating a cancer patient comprising comparing APCDD1 expression in a cancer sample from the patient to APCDD1 expression in a control sample and (1) treating the patient with a composition of the invention if APCDD1 expression is upregulated in the cancer sample as compared to the control sample; or (2) performing a secondary assay if APCDD1 expression is unchanged or downregulated in the cancer sample as compared to the control sample.

In some aspects the invention provides methods of modulating one or more activities in a cell that expresses APCDD1 comprising contacting the cells with an amount of an APCDD1 modulator of the invention effective to modulate the one or more activities.

These and other aspects of the present invention will be elucidated in the detailed description of the invention.

BRIEF DESCRIPTION OF THE DRAWINGS

FIG. 15 depicts an amino acid sequence of APCDD1 (SEQ ID NO:2).

DETAILED DESCRIPTION

Figures 1, 2:
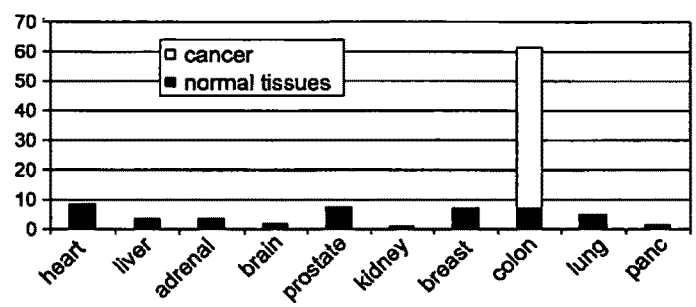
FIG. 1 depicts a graphical representation of relative APCDD1 mRNA levels in normal and cancerous samples.
FIG. 2 depicts gene expression data generated from Affymetrix GeneChip® ((Human Genome U133 Plus 2.0 Array, Affymetrix, Inc.)) oligonucleotide arrays (Affy) and cDNA microarrays synthesized in-house (EVD).

The inventors of the present application have discovered, inter alia, that APCDD1 is over-expressed in several cancers, including lung and colon cancer, and has restricted expression in normal tissues. Surprisingly, inhibition of APCDD1 inhibits cancer cell survival. Further, it has been found that inhibition of APCDD1 modulates levels of APCDD1 downstream markers including cyclin D1. Accordingly, the present invention provides, inter alia, methods and compositions for the treatment, diagnosis and imaging of cancer, in particular for the treatment, diagnosis and imaging of APCDD1-related cancers, as well as for the treatment of other diseases and disorders associated with aberrant expression of APCDD1. These and other aspects of the present invention are provided in the present application.

DEFINITIONS

Various definitions are used throughout this document Most words have the meaning that would be attributed to those words by one skilled in the art. Words specifically defined either below or elsewhere in this document have the meaning provided in the context of the present invention as a whole and as are typically understood by those skilled in the art.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa. Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

As used herein, the singular forms "a," "an" and "the" include plural references unless the content clearly dictates otherwise. Thus, for example, reference to "an antibody" includes a mixture of two or more such antibodies.

As used herein, the term "about" refers to +/−10%, or +/−5% of a value.

As used herein, the term "APCDD1", also known as B7323, B7323N, DRAPC1 and FP7019, refers to a molecule whose expression is downregulated by the tumor suppressor gene, adenopolyposis coli (APC). An exemplary nucleotide sequences of APCDD1 is set forth as SEQ ID NO:1, and an exemplary amino acid sequence of APCDD1 is set forth as SEQ ID NO:2.

Other examples of APCDD1 nucleotide sequences include GenBank accession numbers BC053324.1 (GI:31419785), NM_153000 (GI:30387616), and AB104887 (GI:28866900), each of which is herein incorporated in its entirety. Other examples of APCDD1 amino acid sequences include GenBank accession numbers, Q8J025 (GI:74728445), and BAC65165 (GI:28866901), each of which is herein incorporated in its entirety.

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual", "subject", "host" and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some embodiments the subject is a human.

As used herein, "cancer" refers to primary or metastatic cancers. The term "cancer cells" refers to cells that are transformed. These cells can be isolated from a patient who has cancer, or be cells that are transformed in vitro to become cancerous. Cancer cells can be derived from many types of samples including any tissue or cell culture line. In some embodiments the cancer cells are hyperplasias, tumor cells, or neoplasms. In some embodiments, the cancer cells are isolated from colon tissue, prostate tissue, lung tissue, bladder tissue, kidney tissue, breast tissue, uterine tissue, ovarian tissue, or pancreatic tissue. In some embodiments, the cancer cells are taken from established cell lines that are publicly available. In some embodiments, cancer cells are isolated from pre-existing patient samples or from libraries comprising cancer cells. In some embodiments, cancer cells are isolated and then implanted in a different host, e.g., in a xenograft. In some embodiments cancer cells are transplanted and used in a SCID mouse model. In some embodiments, the cancer is colon, prostate or breast cancer.

As used herein, the term "transformed" refers to any alteration in the properties of a cell that is stably inherited by its progeny. In some embodiments, "transformed" refers to the change of normal cell to a cancerous cell, e.g., one that is capable of causing tumors. In some embodiments, a transformed cell is immortalized. Transformation can be caused by a number of factors, including overexpression of a receptor in the absence of receptor phosphorylation, viral infection, mutations in oncogenes and/or tumor suppressor genes, and/or any other technique that changes the growth and/or immortalization properties of a cell.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, or the like.

As used herein, the term "metastasis" refers to a cancer which has spread to a site distant from the origin of the cancer, e.g. from the primary tumor. Sites of metastasis include without limitation, the bone, lymph nodes, lung, liver, and brain.

As used herein, the term "angiogenesis" refers to the development of blood vessels in a patient.

As used herein, the term "clinical endpoint" refers to a measurable event indicative of cancer. Clinical endpoints include without limitation, time to first metastasis, time to subsequent metastasis, size and/or number of metastases, size and/or number of tumors, location of tumors, aggressiveness of tumors, quality of life, pain and the like. Those skilled in the art are credited with the ability to determine and measure clinical endpoints. Methods of measuring clinical endpoints are known to those of skill in the art.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, saccharides, and lipids.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis.

As used herein, the term "modulator" refers to a composition that modulates one or more physiological or biochemical events associated with cancer. In some embodiments the modulator inhibits one or more biological activities associated with cancer. In some embodiments the modulator is a small molecule, an antibody, a mimetic, a decoy or an oligonucleotide. In some embodiments the modulator acts by blocking, ligand binding or by competing for a ligand-binding site. In some embodiments the modulator acts independently of ligand binding. In some embodiments the modulator does not compete for a ligand binding site. In some embodiments the modulator blocks expression of a gene product involved in cancer. In some embodiments the modulator blocks a physical interaction of two or more biomolecules involved in cancer. In some embodiments modulators of the invention inhibit one or more APCDD1 activities selected from the group consisting of cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis. In some embodiments, the APCDD1 modulator inhibits APCDD1 expression.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In some embodiments, if the gene product is proteinaceous, it exhibits a biological activity. In some embodiments, if the gene product is a nucleic acid, it can be translated into a proteinaceous gene product that exhibits a biological activity. The level of a polypeptide can be regulated by cellular processes that influence the translational efficiency and/or the stability of the corresponding mRNA.

"Translational efficiency", as used herein, refers to the rate at which an mRNA is decoded to produce a specific polypeptide according to the rules specified by the genetic code. In some embodiments, an APCDD1 modulator can reduce the translational efficiency of the APCDD1 mRNA.

"mRNA stability", as used herein, refers to the ability of an mRNA to resist the action of RNAses that degrade the mRNA. Processes or agents that alter the stability of an mRNA can alter the amount of protein that is synthesized via that mRNA. In some embodiments, an APCDD1 modulator can reduce the stability of the APCDD1 mRNA.

"Modulation of APCDD1 activity", as used herein, refers to an increase or decrease in an APCDD1 activity that can be a result of for example, interaction of an agent with an APCDD1 polynucleotide or polypeptide, inhibition of APCDD1 transcription and/or translation (e.g., through antisense or siRNA interaction with the APCDD1 gene or APCDD1 gene expression product, through modulation of transcription factors that facilitate APCDD1 expression), and the like. For example, modulation of an APCDD1 activity refers to an increase in a biological activity or a decrease in a biological activity. Modulation of APCDD1 activity also refers to increasing or decreasing one or more APCDD1 phenotypes. APCDD1 phenotypes include, without limitation, APCDD1-dependent changes in cell proliferation, cell growth, anchorage-independent growth, tumorigenicity, cell cycle regulation, cancer cell motility, cell adhesion, tumor formation, metastasis, cancer cell survival, and cyclin production. APCDD1 activity can be assessed by means including, without limitation, assessing APCDD1 polypeptide levels, or by assessing APCDD1 transcription levels. Comparisons of APCDD1 activity can also be accomplished by measuring levels of an APCDD1 downstream marker, measuring cell proliferation, measuring cell growth, measuring anchorage-independent growth, measuring tumorigenicity, measuring cell cycle regulation, measuring cancer cell motility, measuring cell adhesion, measuring tumor formation, measuring metastasis, measuring cancer cell survival, measuring cyclin production, measuring cancer cell survival, measuring cell signaling activity, measuring tumorigenicity, measuring metastasis, measuring cell-to-cell interactions including interactions between APCDD1 and other cell-membrane proteins, and measuring angiogenesis, among others.

In some embodiments, inhibition of APCDD1 activity is of particular interest. As used herein, the term "inhibit" refers to a reduction, decrease, inactivation or down-regulation of an activity or quantity. For example, in the context of the present invention, APCDD1 modulators may inhibit one or more of cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis. Inhibition of such activities may be at least 20%, at least 25%, at least 50%, at least 70%, at least 75%, at least 80%, at least 90%, at least 95%, at least 97%, at least 98%, at least 99%, or 100%, as compared to a control. Those of skill in the art are credited with the ability to measure APCDD1 modulation; a non-limiting list of exemplary assays is set forth below.

Accordingly, as used herein, the term "inhibition of APCDD1" refers to a reduction, decrease, inactivation or down-regulation of one or more APCDD1-mediated biological activities. Inhibition of an "APCDD1 biological activity" refers to a reduction, decrease, inactivation, or down-regulation of for example, cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis. Inhibition of such activities may be at least 20%, at least 25%, at least 50%, at least 70%, at least 75%, at least 80%, at least 90%, at least 95%, at least 97%, at least 98%, at least 99%, or 100%, as compared to a control.

In some embodiments, modulation of APCDD1 activities that activate or result in an increase of APCDD1 activity is of particular interest. Activation, upregulation or increases in the APCDD1 activity may be at least 125%, at least 150%, at least 200%, at least 250%, at least 300%, at least 500% as compared to a control. For example, an APCDD1 modulator that increases cell death 200% has increased cell death twofold as compared to a control lacking the APCDD1 modulator.

As used herein, the term "differentially expressed in a cancer cell" and "a polynucleotide that is differentially expressed in a cancer cell" are used interchangeably herein, and refer to a polynucleotide that represents or corresponds to a gene that is differentially expressed in a cancerous cell when compared with a cell of the same cell type that is not cancerous, e.g., mRNA is found at levels at least about 25%, at least about 50% to about 75%, at least about 90%, at least about 1.5-fold, at least about 2-fold, at least about 5-fold, at least about 10-fold, or at least about 50-fold or more, different (e.g., higher or lower). The comparison can be made in tissue, for example, if one is using in situ hybridization or another assay method that allows some degree of discrimination among cell types in the tissue. The comparison may also or alternatively be made between cells removed from their tissue source, or between one cell in situ and a second cell removed from its tissue source. In some embodiments, the gene is upregulated in the cancer gene as compared to the normal cell.

An APCDD1 associated-cancer is "inhibited" if at least one symptom of the cancer is alleviated, terminated, slowed, or prevented. As used herein, an APCDD1 associated-cancer is also "inhibited" if recurrence or metastasis of the cancer is reduced, slowed, delayed, or prevented.

As used herein, the phrase "inhibits cancer cell growth" refers to a decrease, reduction, or abolition of cancer cell growth in the presence of an APCDD1 modulator wherein the cell expresses APCDD1. In some embodiments the cells differentially express APCDD1 relative to other normal cells and/or relative to other cancer cells. In this context, cell growth can be decreased by an APCDD1 modulator by at least 25%, at least 50%, at least 75%, at least 85%, at least 90%, at least 95%, up to 100% relative to cancer cell growth in the absence of an APCDD1 modulator. Comparisons of cancer cell growth can be accomplished using, for example, MTT assay (for example, the Vybrant® MTT Cell Proliferation Assay Kit (Invitrogen)); BrdU incorporation (for example the Absolute-S SBIP assay (Invitrogen)); measuring intracellular ATP levels (for example using ATPLite™-M, 1,000 Assay Kit (PerkinElmer) or ATP Cell Viability Assay Kit (BioVision)); DiOc18 assay, a membrane permeable dye (Invitrogen); Glucose-6-phosphate dehydrogenase activity assay (for example, the Vibrant cytotoxicity assay (Invitrogen)); or measuring cellular LDH activity.

As used herein, the phrase "inhibits cyclin D1" refers to a decrease, reduction, or abolition of APCDD1-mediated cyclin production. In this context, APCDD1 mediated cyclin production can be decreased by an inhibitory agent by at least 25%, at least 50%, at least 75%, at least 85%, at least 90%, at least 95%, up to 100% relative to APCDD1 mediated cyclin production in the absence of an APCDD1 modulator. Comparisons of cyclin production can be accomplished by measuring, for example, cyclin mRNA levels via RT-PCR or northern blotting; cyclin polypeptide levels via immunoblotting, immunoprecipitation or ELISA; or using functional assays, including co-immunoprecipitation assays to measure levels of cyclin that are complexed with cyclin regulators such as cyclin-dependent kinases (CDK's) using for example antibodies that target CDK, p21WAF1, p27 KIP-1; and measuring phosphorylation of cyclins by the CDK's can be assayed through radiolabeling and immunoprecipitation analysis or FRET-based methods, for example, CDK2/Cyclin A Assay Kit (Molecular Devices).

As used herein, the phrases "inhibits proliferation" refers to decreasing, reducing, or abolishing APCDD1-mediated proliferation and can be measured via a number of methods known to those of skill in the art. Cell proliferation assays include, without limitation, MTT assays (for example, the Vybrant® MTT Cell Proliferation Assay Kit (Invitrogen)); BrdU incorporation assays (for example, the Absolute-S SBIP assay (Invitrogen)); measuring intracellular ATP levels (commercial versions of the assay include ATPLite™-M, 1,000 Assay Kit (PerkinElmer) and ATP Cell Viability Assay Kit (BioVision)); DiOc18 assay, a membrane permeable dye (Invitrogen); Glucose-6-phosphate dehydrogenase activity assay (for example, the Vibrant cytotoxicity assay (Invitrogen)); measuring cellular LDH activity; and $^3$H-thymidine incorporation and the Cell Titer Glo Assay (Promega).

As used herein, the phrase "inhibits progression through the cell cycle" refers to slowing or stalling the cell division. Cell-cycle progression can be assayed by bromodeoxyuridine (BRDU) incorporation. Such assays identify a cell population undergoing DNA synthesis by incorporation of BRDU into newly synthesized DNA. Newly-synthesized DNA may then be detected using an anti-BRDU antibody (Hoshino et al., 1986, int. J. Cancer 38, 369; Campana et al., 1988, J. Immunol. Meth. 107, 79), or by other means. Cell proliferation can also be assayed by phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem. 270:20098-105). Cell proliferation can also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA synthesis. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L at al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available and include the Promega CellTiter 96® AQueous Non-Radioactive Cell Proliferation Assay (Cat#G5421). Cell proliferation can also be assayed by colony formation in soft agar (Sambrook at al., Molecular Cloning, Cold Spring Harbor (1989)). Cell proliferation may also be assayed by measuring ATP levels as indicator of metabolically active cells. Such assays are commercially available and include Cell Titer-Glo™ ((Promega). Cell cycle proliferation can also be assayed by flow cytometry (Gray J W at al. (1986) Int J Radiat Biol Relat Stud Phys Chem Med 49:237-55). Cells may be stained with propidium iodide and evaluated in a flow cytometer to measure accumulation of cells at different stages of the cell cycle.

An "APCDD1 downstream marker", as used herein, is a gene or activity which exhibits altered level of expression in a cancer tissue or cancer cell compared to its expression level in normal or healthy tissue, or is a property altered in the presence of an APCDD1 modulator. In some embodiments, the downstream markers exhibit altered levels of expression when APCDD1 is perturbed with an APCDD1 modulator of the present invention. APCDD1 downstream markers include, without limitation, cyclin D1.

As used herein, the term "up-regulates" refers to an increase, activation or stimulation of an activity or quantity.

As used herein, the term "N-terminus" refers to the first 10 amino acids of a protein.

As used herein, the term "C-terminus" refers to the last 10 amino acids of a protein.

The term "domain" as used herein refers to a structural part of a biomolecule that contributes to a known or suspected function of the biomolecule. Domains may be co-extensive with regions or portions thereof and may also incorporate a portion of a biomolecule that is distinct from a particular region, in addition to all or part of that region.

As used herein, the term "extracellular domain" refers to the portion of a molecule that is outside or external to a cell. In the context of the present invention, an N-terminal extracellular domain refers to the extracellular domain that is present at the N-terminus of the molecule immediately before the transmembrane domain.

As used herein, the term "ligand binding domain" refers to any portion or region of a receptor retaining at least one qualitative binding activity of a corresponding native sequence of APCDD1.

The term "region" refers to a physically contiguous portion of the primary structure of a biomolecule. In the case of proteins, a region is defined by a contiguous portion of the amino acid sequence of that protein. In some embodiments, a "region" is associated with a function of the biomolecule.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity. In the context of the present invention, APCDD1 polypeptide fragments do not comprise the entire APCDD1 polypeptide sequence set forth in SEQ ID NO:2. In some embodiments, APCDD1 fragments retain one or more activities of native APCDD1.

As used herein, the phrase "APCDD1-related cells/tumors/samples" and the like refers to cells, samples, tumors or other pathologies that are characterized by differential expression of APCDD1 relative to non-cancerous and/or non-metastatic cells, samples, tumors, or other pathologies. In some embodiments, APCDD1-related cells, samples, tumors or other pathologies are characterized by increased APCDD1 expression relative to non-metastatic cells, samples, tumors, or other pathologies.

As used herein, the term "antibody" refers to monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof; and also include antibody fragments, including Fab, Fab', F(ab')$_2$, scFv, Fv, camelbodies, or microantibodies. An antibody can also refer to an anti-idiotype antibody, i.e., an antibody directed against the antigen specific part of the sequence of an antibody and thus recognizes the binding sites of other antibodies; or an anti-anti-idiotype antibody, i.e., an antibody with a combining site that mimics the epitope on the antigen that was used to generate the original antibody. The term "antibody" further includes in vivo therapeutic antibody gene transfer.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature, 352:624-628 (1991) and Marks at al, J. Mol. Biol., 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, in some embodiments comprising the antigen-binding or variable region thereof. Examples of antibody fragments include Fab, Fab', F(ab)$_2$, and Fv fragments; diabodies; linear antibodies (Zapata at al., Protein Eng. 8(10): 1057-1062 [1995]); single-chain antibody molecules; and multispecific antibodies formed from antibody fragment(s).

An "intact" antibody is one that comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In some embodiments the intact antibody has one or more effector functions.

Antibody "effector functions" refer to those biological activities attributable to the Fc region (a native sequence Fc region or amino acid sequence variant Fc region) of an antibody. Examples of antibody effector functions include C1q binding complement dependent cytotoxicity; Fc receptor binding antibody-dependent cell-mediated cytotoxicity (ADCC); phagocytosis; down regulation of cell surface receptors (e.g. B cell receptor; BCR), etc.

"Antibody-dependent cell-mediated cytotoxicity" or "ADCC" refers to a form of cytotoxicity in which secreted Ig bound onto Fc receptors (FeEs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Human effector cells" are leukocytes that express one or more FcRs and perform effector functions. In some embodiments the cells express at least FcγRIII and perform ADCC effector function. Examples of human leukocytes that mediate ADCC include peripheral blood mononuclear cells (PBMC), natural killer (NK) cells, monocytes, cytotoxic T cells and neutrophils. The effector cells may be isolated from a native source thereof, e.g. from blood or PBMCs as described herein.

The terms "Fc receptor" or "FcR" are used to describe a receptor that binds to the Fc region of an antibody. In some embodiments the FcR is a native sequence human FcR. Moreover, in some embodiments the FcR is one that binds an IgG antibody (a gamma receptor) and includes receptors of the FcγRI, FcγFIII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review in Daron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas at al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer at al., J. Immunol. 117:587 (1976) and Kim at a., J. Immunol. 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

As used herein, the term "epitope" refers to an antigenic determinant of a polypeptide. In some embodiments an epitope may comprise 3 or more amino acids in a spatial conformation which is unique to the epitope. In some embodiments epitopes are linear or conformational epitopes. Generally an epitope consists of at least 4, at least 6, at least 8, at least 10, and at least 12 such amino acids, and more usually, consists of at least 8-10 such amino acids. Methods of determining the spatial conformation of amino acids are known in the art, and include, for example, x-ray crystallography and 2-dimensional nuclear magnetic resonance.

The phrase "complementarity determining region" refers to amino acid sequences which together define the binding affinity and specificity of the natural Fv region of a native immunoglobulin binding site. See, e.g., Chothia et al., J. Mol. Biol. 196:901-917 (1987); Kabat et al., U.S. Dept, of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu. One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region that disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which are incorporated herein by reference.

A wide variety of antibody/immunoglobulin frameworks or scaffolds can be employed so long as the resulting polypeptide includes at least one binding region that is specific for the target protein. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

One can generate non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target. Such compounds are known herein as "polypeptides comprising a target-specific binding region". Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Sco; Proteins GmbH, Halle, Germany).

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

The term "antagonist" is used in the broadest sense, and includes any molecule that partially or fully blocks, inhibits, or neutralizes a biological activity of a tumor cell antigen disclosed herein. In a similar manner, the term "agonist" is used in the broadest sense and includes any molecule that mimics a biological activity of a tumor cell antigen disclosed herein. Suitable agonist or antagonist molecules specifically include agonist or antagonist antibodies or antibody fragments, fragments or amino acid sequence variants of tumor cell antigens, peptides, antisense oligonucleotides, small organic molecules, etc. Methods for identifying agonists or antagonists of a tumor cell antigen may comprise contacting a tumor cell expressing the antigen of interest with a candidate agonist or antagonist molecule and measuring a detectable change in one or more biological activities normally associated with the tumor cell antigen. The antagonist may also be a peptide generated by rational design or by phage display (see, e.g., WO98/35036 published 13 Aug. 1998). In one embodiment, the molecule of choice may be a "CDR mimic" or antibody analogue designed based on the CDRs of an antibody. While such peptides may be antagonistic by themselves, the peptide may optionally be fused to a cytotoxic agent so as to add or enhance antagonistic properties of the peptide.

As used herein, the term "oligonucleotide" refers to a series of linked nucleotide residues. Oligonucleotides include without limitation, antisense and siRNA oligonucleotides. Oligonucleotides comprise portions of a DNA sequence and have at least about 10 nucleotides and as many as about 500 nucleotides. In some embodiments oligonucleotides comprise from about 10 nucleotides to about 50 nucleotides, from about 15 nucleotides to about 30 nucleotides, and from about 20 nucleotides to about 25 nucleotides. Oligonucleotides may be chemically synthesized and can also be used as probes. In some embodiments oligonucleotides are single stranded. In some embodiments oligonucleotides comprise at least one portion which is double stranded. In some embodiments the oligonucleotides are antisense oligonucleotides (ASO). In some embodiments the oligonucleotides are RNA interference oligonucleotides (RNAi oligonucleotides).

As used herein, the term "antisense oligonucleotide" refers to an unmodified or modified nucleic acid having a nucleotide sequence complementary to an APCDD1 polynucleotide sequence including polynucleotide sequences associated with the transcription or translation of APCDD1 (e.g., a promoter of an APCDD1 polynucleotide), where the antisense polynucleotide is capable of hybridizing to an APCDD1 polynucleotide sequence. Of particular interest are antisense polynucleotides capable of inhibiting transcription and/or translation of APCDD1 polypeptide-encoding polynucleotide either in vitro or in vivo.

As used herein, the terms "siRNA oligonucleotides", "RNAi oligonucleotides", "short interfering RNA", or "siRNA" are used interchangeably and refer to oligonucleotides that work through post-transcriptional gene silencing, also known as RNA interference (RNAi). The terms refer to a double stranded nucleic acid molecule capable of RNA interference "RNAi", (see Kreutzer at al., WO 00/44895; Zernicka-Goetz et al. WO 01/36646; Fire, WO 99/32619; Mello and Fire, WO 01/29058). siRNA molecules are generally RNA molecules but further encompass chemically modified nucleotides and non-nucleotides. SiRNA gene-targeting experiments have been carried out by transient siRNA transfer into cells (achieved by such classic methods as liposome-mediated transfection, electroporation, or microinjection). Molecules of siRNA are 21- to 23-nucleotide RNAs, with characteristic 2- to 3-nucleotide 3'-overhanging ends resembling the RNase III processing products of long double-stranded RNAs (dsRNAs) that normally initiate RNAi.

As used herein, the term "decoy receptor" refers to a receptor comprising at least a portion of a polypeptide, mimetic, or other macromolecule capable of binding an APCDD1 ligand. As used herein, the term "therapeutically effective amount" is meant to refer to an amount of a medicament which produces a medicinal effect observed as reduction or reverse in one or more clinical endpoints, growth and/or survival of cancer cell, or metastasis of cancer cells in an individual when a therapeutically effective amount of the medicament is administered to the individual. Therapeutically effective amounts are typically determined by the effect they have compared to the effect observed when a composition which includes no active ingredient is administered to a similarly situated individual. The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician.

As used herein, the terms "in combination with" or "in conjunction with" refer to administration of the APCDD1 modulators of the invention with other therapeutic regimens.

As used herein, the term "susceptible" refers to patients for whom APCDD1 therapy is an acceptable method of treatment, i.e., patients who are likely to respond positively. In some embodiments, cancer patients susceptible to APCDD1 therapy express high levels of APCDD1 relative to those patients not susceptible to APCDD1 therapy. In some embodiments, cancer patients who are not good candidates for APCDD1 therapy include cancer patients with tumor samples that lack or have lower levels of APCDD1 in or on their cancer cells.

As used herein, the term "detecting" means to establish, discover, or ascertain evidence of an activity (for example, gene expression) or biomolecule (for example, a polypeptide).

A "native sequence" polypeptide is one that has the same amino acid sequence as a polypeptide derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70%, at least about 80% homology or at least about 90% homology with at least one receptor binding domain of a native ligand or with at least one ligand binding domain of a native receptor or ligand binding domains thereof. The amino acid sequence variants possess substitutions, deletions, and/or insertions at certain positions within the amino acid sequence of the native amino acid sequence.

As used herein, the phrase "homologous nucleotide sequence," or "homologous amino acid sequence," or variations thereof refers to sequences characterized by a homology, at the nucleotide level or amino acid level, of at least a specified percentage and is used interchangeably with "sequence identity". Homologous nucleotide sequences include those sequences coding for isoforms of proteins. Such isoforms can be expressed in different tissues of the same organism as a result of for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity.

Percent homology or identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, homology between the probe and target is between about 70% to about 80%. In some embodiments, nucleic acids have nucleotides that are about 85%, about 90%, about 92%, about 94%, about 95%, about 97%, about 98%, about 99% and about 100% homologous to SEQ ID NO:1, or a portion thereof.

Homology may also be at the polypeptide level. In some embodiments, polypeptides are about 85%, about 90%, about 92%, about 94%, about 95%, about 97%, about 98%, about 99% and about 100% homologous to SEQ ID NO:2, or a portion thereof.

As used herein, the term "probe" refers to nucleic acid sequences of variable length. In some embodiments probes comprise at least about 10 and as many as about 6,000 nucleotides. In some embodiments probes comprise at least 12, at least 14, at least 16, at least 18, at least 20, at least 25, at least 50 or at least 75 consecutive nucleotides. Probes are used in the detection of identical, similar, or complementary nucleic acid sequences. Longer length probes are usually obtained from natural or recombinant sources, are highly specific to the target sequence, and are much slower to hybridize to the target than are oligomers. Probes may be single- or double-stranded and are designed to have specificity in PCR, hybridization membrane-based, in situ hybridization (ISH), fluorescent in situ hybridization (FISH), or FT ISA-like technologies.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein the term "isolated" refers to a polynucleotide, a polypeptide, an antibody, or a host cell that is in an environment different from that in which the polynucleotide, the polypeptide, or the antibody naturally occurs. Methods of isolating cells are well known to those skilled in the art. A polynucleotide, a polypeptide, or an antibody which is isolated is generally substantially purified.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

As used herein, the term "binding" means the physical or chemical interaction between two or more biomolecules or compounds. Binding includes ionic, non-ionic, hydrogen bonds, Van der Waals, hydrophobic interactions, etc. Binding can be either direct or indirect; indirect being through or due to the effects of another biomolecule or compound. Direct binding refers to interactions that do not take place through or due to the effect of another molecule or compound but instead are without other substantial chemical intermediates.

As used herein, the term "contacting" means bringing together, either directly or indirectly, one molecule into physical proximity to a second molecule. The molecule can be in any number of buffers, salts, solutions, etc. "Contacting" includes, for example, placing a polynucleotide into a beaker, microtiter plate, cell culture flask, or a microarray, or the like, which contains a nucleic acid molecule. Contacting also includes, for example, placing an antibody into a beaker, microtiter plate, cell culture flask, or microarray, or the like, which contains a polypeptide. Contacting may take place in vivo, ex vivo, or in vitro.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point (TO for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

As used herein, the term "moderate stringency conditions" refers to conditions under which a probe, primer, or oligonucleotide will hybridize to its target sequence, but to a limited number of other sequences. Moderate conditions are sequence-dependent and will be different in different circumstances. Moderate conditions are well-known to the art skilled and are described in, inter alfa, Maniatis et al. (Molecular Cloning: A Laboratory Manual, Cold Spring Harbor Laboratory, 2nd Edition (December 1989)).

The nucleic acid compositions described herein can be used, for example, to produce polypeptides, as probes for the detection of mRNA in biological samples (e.g., extracts of human cells) or cDNA produced from such samples, to generate additional copies of the polynucleotides, to generate ribozymes or oligonucleotides (single and double stranded), and as single stranded DNA probes or as triple-strand forming oligonucleotides. The probes described herein can be used to, for example, determine the presence or absence of the polynucleotides provided herein in a sample. The polypeptides can be used to generate antibodies specific for a polypeptide associated with cancer, which antibodies are in turn useful in diagnostic methods, prognostic methods, and the like as discussed in more detail herein. Polypeptides are also useful as targets for therapeutic intervention, as discussed in more detail herein. Antibodies of the present invention may also be used, for example, to purify, detect, and target the polypeptides of the present invention, including both in vitro and in vivo diagnostic and therapeutic methods. For example, the antibodies are useful in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988). These and other uses are described in more detail below.

As used herein the term "imaging agent" refers to a composition linked to an antibody, small molecule, or probe of the invention that can be detected using techniques known to the art-skilled. As used herein, the term "evidence of gene expression" refers to any measurable indicia that a gene is expressed.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Specific examples of cancers that can be treated by the methods and compositions of the present invention include, but are not limited to, APCDD1 associated cancers. As used herein, "APCDD1 associated cancer" refers to a cancer characterized by cells that differentially express APCDD1 relative to non-cancerous cells. The present invention is also applicable to any tumor cell-type where APCDD1 plays a role in cell proliferation, cell growth, anchorage-independent growth, tumorigenicity, cell cycle regulation, cancer cell motility, cell adhesion, tumor formation, metastasis, cancer cell survival, and cyclin production. In some embodiments, the cancer is colon, prostate, breast cancer or a cancer metastasis. In some embodiments, the cancer is colon or prostate cancer. In some embodiments, such cancers exhibit differential expression of APCDD1 of at least about 20%, at least about 25%, at least about 50%, at least about 100%, at least about 150%, at least about 200%, at least about 300%, at least about 500% or more as compared to a control.

The present invention provides methods and compositions that provide for the treatment, inhibition, and management of diseases and disorders associated with APCDD1 overexpression as well as the treatment, inhibition, and management of symptoms of such diseases and disorders. Some embodiments of the invention relate to methods and compositions comprising compositions that treat, inhibit or manage cancer including, without limitation, cancer metastases, cancer cell survival, cancer cell proliferation, cancer cell growth, cell cycle regulation, and cancer cell invasiveness.

The present invention further provides methods including other active ingredients in combination with the APCDD1 modulators of the present invention. In some embodiments, the methods further comprise administering one or more conventional cancer therapeutics to the patient. In some embodiments the methods of the present invention further comprise treating the patient with one or more of chemotherapy, radiation therapy or surgery.

The present invention also provides methods and compositions for the treatment, inhibition, and management of cancer or other hyperproliferative cell disorder or disease that has become partially or completely refractory to current or standard cancer treatment, such as surgery, chemotherapy, radiation therapy, hormonal therapy, and biological therapy.

The invention also provides diagnostic and/or imaging methods using the APCDD1 modulators of the invention, particularly APCDD1 antibodies, to diagnose cancer and/or predict cancer progression. In some embodiments, the methods of the invention provide methods of imaging and localizing tumors and/or metastases and methods of diagnosis and prognosis. In some embodiments, the methods of the invention provide methods to evaluate the appropriateness and/or effectiveness of APCDD1-related therapy.

APCDD1 Modulators

The present invention provides APCDD1 modulators for, inter alfa, the treatment, diagnosis, detection or imaging of cancer. APCDD1 modulators are also useful in the preparation of medicaments for the treatment of cancer. In some embodiments the APCDD1 modulator is an APCDD1 inhibitor.

In some embodiments, the APCDD1 modulator is a nucleotide, a small molecule, a mimetic, a decoy, or an antibody. In some embodiments the APCDD1 modulator is an isolated double-stranded RNA (dsRNA); an isolated oligonucleotide comprising at least 10 consecutive nucleotides of SEQ ID NO:1, in some embodiments selected from the group consisting of SEQ ID NOs:5-21, 24 and 25; an antibody that binds an epitope in a domain of APCDD1 selected from the group consisting of the extracellular domain, a small molecule; a mimetic; a soluble receptor, or a decoy.

In some embodiments, the APCDD1 modulator inhibits an APCDD1 activity by at least 20%, 50%, 75%, 90%, 95%, 97%, 98%, 99% or 100%, as compared to a control. In some embodiments, the APCDD1 modulator inhibits cyclin D1 expression by at least 25%, 50%, 75%, 90%, 95%, 97%, 98%, 99% or 100%, as compared to a control.

Antibodies

In some embodiments the APCDD1 modulator is a monoclonal antibody, a polyclonal antibody, a chimeric antibody, a human antibody, a humanized antibody, a single-chain antibody, an Fab fragment or an anti-anti-idiotype antibody. The antibody or Fab fragment may be labeled with, for example, an enzyme, radioisotope, or fluorophore. In some embodiments the antibody or Fab fragment has a binding affinity less than about $1 \times 10^5$ Ka for a polypeptide other than APCDD1. In some embodiments, the APCDD1 modulator is a monoclonal antibody which binds to APCDD1 with an affinity of at least $1 \times 10^8$ Ka.

The invention also provides antibodies that competitively inhibit binding of an antibody to an epitope of the invention as determined by any method known in the art for determining competitive binding using, for example, immunoassays. In some embodiments, the antibody competitively inhibits binding to the epitope by at least 95%, at least 90%, at least 85%, at least 80%, at least 75%, at least 70% or at least 50%.

In some embodiments the antibody is a humanized antibody. Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-hie surface by replacement of surface residues (a process referred to in the art as "veneering"). In the present invention, humanized antibodies will include both "humanized" and "veneered" antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison at al., Proc. Natl. Acad. Sci, 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7): 773-83 (1991) each of which is incorporated herein by reference.

Antibodies of the present invention may function through different mechanisms. In some embodiments, antibodies trigger antibody-dependent cellular cytotoxicity (ADCC), a lytic attack on antibody-targeted cells. In some embodiments, antibodies have multiple therapeutic functions, including, for example, antigen-binding, induction of apoptosis, and complement-dependent cellular cytotoxicity (CDC). In some embodiments, the antibody or is conjugated to a toxin or radionuclide.

In some embodiments, antibodies of the present invention may act as APCDD1 antagonists. For example, in some embodiments the present invention provides antibodies which disrupt the receptor/ligand interactions with the polypeptides of the invention either partially or fully. In some embodiments antibodies of the present invention bind an epitope disclosed herein, or a portion thereof. In some embodiments, antibodies are provided that modulate ligand activity or receptor activity by at least 95%, at least 90%, at least 85%, at least 80%, at least 75%, at least 70% or at least 50% compared to the activity in the absence of the antibody.

In some embodiments the present invention provides neutralizing antibodies. A neutralizing antibody binds an infectious agent, such as a virus or a bacterium, such as a virus or bacterium associated with cancer (e.g., a JC polyoma virus, Epstein-Barr virus, or *Helicobacter pylori*). In some embodiments the neutralizing antibodies can effectively act as receptor antagonists, i.e., inhibiting either all or a subset of the biological activities of the ligand-mediated receptor activation. In some embodiments the antibodies may be specified as agonists, antagonists or inverse agonists for biological activities comprising the specific biological activities of the peptides of the invention disclosed herein.

In some embodiments the antibodies inhibit one or more APCDD1 activities selected from the group consisting of cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis. The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

In addition to chimeric and humanized antibodies, fully human antibodies can be derived from transgenic mice having human immunoglobulin genes (see, e.g., U.S. Pat. Nos. 6,075,181, 6,091,001, and 6,114,598, all of which are incorporated herein by reference), or from phage display libraries of human immunoglobulin genes (see, e.g. McCafferty at al., Nature, 348:552-554 (1990). Clackson at al., Nature, 352: 624-628 (1991), and Marks et al., J. Mol. Biol., 222:581-597 (1991)). In some embodiments, antibodies may be produced and identified by scFv-phage display libraries. Antibody phage display technology is available from commercial sources such as from Morphosys.

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, in some embodiments in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial or limiting dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas for expression, antibodies can be produced in a cell line such as a CHO or myeloma cell line, as disclosed in U.S. Pat. Nos. 5,545,403; 5,545,405; and 5,998,144; each incorporated herein by reference. Briefly the cell line is transfected with vectors capable of expressing a light chain and a heavy chain, respectively. By transfecting the two proteins on separate vectors, chimeric antibodies can be produced. Immunol. 147:8; Banchereau et al. (1991) Clin. Immunol. Spectrum 3:8; and Banchereau at al. (1991) Science 251:70; all of which are herein incorporated by reference.

Human antibodies can also be produced using techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole at al., Monoclonal Antibodies and Cancer Therapy, Alan R. Liss, p. 77 (1985) and Boerner at al., J. Immunol., 147(1):86 95 (1991)). Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779 783 (1992); Lonberg at al., Nature 368 856 859 (1994); Morrison, Nature 368, 812 13 (1994); Fishwild at al., Nature Biotechnology 14, 845 51 (1996); Neuberger, Nature Biotechnology 14, 826 (1996); Lonberg and Huszar, Intern. Rev. Immunol. 13 65 93 (1995); Jones at al., Nature 321:522-525 (1986); Morrison at al., Proc. Natl. Acad. Sci, U.S.A., 81:6851-6855 (1984); Morrison and Oi, Adv. Immunol., 44:65-92 (1988); Verhoeyer at al., Science 239:1534-1536 (1988); Padlan, Molec. Immun. 28:489-498 (1991); Padlan, Molec. Immunol. 31(3):169-217 (1994); and Kettleborough, C. A. at al., Protein Eng. 4(7): 773-83 (1991) each of which is incorporated herein by reference. Fully humanized antibodies can be identified in screening assays using commercial resources such as Morphosys (Martinsried/Planegg, Germany).

Human antibodies can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Antibodies of the present invention can also be produced using human engineering techniques as discussed in U.S. Pat. No. 5,766,886, which is incorporated herein by reference.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

Antibodies of the present invention may be administered to a subject via in vivo therapeutic antibody gene transfer as discussed by Fang et al. (2005), Nat Biotechnol. 23, 584-590. For example recombinant vectors can be generated to deliver a multicistronic expression cassette comprising a peptide that mediates enzyme independent, cotranslational self cleavage of polypeptides placed between MAb heavy and light chain encoding sequences. Expression leads to stoichiometric amounts of both MAb chains. In some embodiments the peptide that mediates enzyme independent, cotranslational self cleavage is the foot-and-mouth-disease derived 2A peptide.

Fragments of antibodies are suitable for use in the methods of the invention so long as they retain the desired affinity of the full-length antibody. Thus, a fragment of an anti-APCDD1 antibody will retain an ability to bind to APCDD1. Such fragments are characterized by properties similar to the corresponding full-length anti-APCDD1 antibody, that is, the fragments will specifically bind a human APCDD1 antigen expressed on the surface of a human cell.

In some embodiments, the antibodies specifically bind to one or more epitopes in an extracellular domain of APCDD1. In some embodiments, the antibodies modulate one or more APCDD1 related biological activities. In some embodiments the antibodies inhibit one or more of cell proliferation, cell growth, anchorage-independent growth, tumorigenicity, cell cycle regulation, cancer cell motility, cell adhesion, tumor formation, metastasis, cancer cell survival, cyclin production, cancer cell survival, cell signaling activity, tumorigenicity, metastasis, cell-to-cell interactions including interactions between APCDD1 and other cell-membrane proteins, and angiogenesis.

In some embodiments the antibody is a monoclonal antibody or Fab fragment which specifically binds to one or more APCDD1 epitopes in a domain selected from the group consisting of the extracellular domain.

In some embodiments, the APCDD1 modulator is a monoclonal antibody or Fab fragment which specifically binds to one or more epitopes in the extracellular domain (ECD) of APCDD1. In some embodiments, the APCDD1 modulator is a monoclonal antibody or Fab fragment which specifically binds to one or more epitopes of SEQ ID NO:2. In some the antibody or Fab fragment specifically binds to an epitope including at least 6 contiguous amino acids of a sequence selected from the group consisting of SEQ ID NOs: 3, 4, 22 and 23.

Suitable antibodies according to the present invention can recognize linear or conformational epitopes, or combinations thereof. In some embodiments the antibodies of the present invention specifically bind to epitopes of antigenic regions of SEQ ID NO:2. In some the antibodies specifically bind to an epitope of an antigenic region of SEQ ID NO:2 wherein the epitope comprises at least 6 contiguous amino acids of a sequence selected from the group consisting of SEQ ID NOs: 3, 4, 22 and 23. In some embodiments the antibody is specific for an epitope having a sequence selected from the group consisting of SEQ ID NOs: 3, 4, 22 and 23.

It is to be understood that these peptides may not necessarily precisely map to one epitope, but may also contain an APCDD1 sequence that is not immunogenic.

Methods of predicting other potential epitopes to which an antibody of the invention can bind are well-known to those of skill in the art and include without limitation, Kyte-Doolittle Analysis (Kyte, J. and Dolittle, R. F., J. Mol. Biol. (1982) 157:105-132), Hopp and Woods Analysis (Hopp, T. P. and Woods, K. R., Proc. Natl. Acad. Sci. USA (1981) 78:3824-3828; Hopp, T. J. and Woods, K. R., Mol. Immunol. (1983) 20:483-489; Hopp, T. J., J. Immunol. Methods (1986) 88:1-18.), Jameson-Wolf Analysis (Jameson, B. A. and Wolf, H., Comput. Appl. Biosci. (1988) 4:181-186.), and Emini Analysis (Emini, E. A., Schliet W. A., Colonno, R. J. and Wimmer, E., Virology (1985) 140:13-20.). In some embodiments, potential epitopes are identified by determining theoretical extracellular domains. Analysis algorithms such as TMpred (see K. Hofmann & W. Stoffel (1993) TMbase—A database of membrane spanning proteins segments Biol. Chem. Hoppe-Seyler 374,166) or TMHMM (A. Krogh, B. Larsson, G. von Heijne, and E. L. L. Sonnhammer. Predicting transmembrane protein topology with a hidden Markov model: Application to complete genomes. Journal of Molecular Biology, 305(3):567-580, January 2001) can be used to make such predictions. Other algorithms, such as SignalP 3.0 (Bednsten et al, (2004) J Mol. Biol. 2004 Jul. 16; 340(4):783-95) can be used to predict the presence of signal peptides and to predict where those peptides would be cleaved from the full-length protein. The portions of the proteins on the outside of the cell can serve as targets for antibody interaction.

Antibodies are defined to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard analysis (Scatchard, Ann. NY Acad. Sci. 51: 660-672, 1949). In some embodiments the antibodies of the present invention bind to their target epitopes or mimetic decoys at least 1.5-fold, 2-fold, 5-fold, 10-fold, 100-fold, $10^3$-fold, $10^4$-fold, $10^3$-fold, $10^6$-fold or greater for the target cancer-associated polypeptide than to other proteins predicted to have some homology to APCDD1.

In some embodiments the antibodies bind with high affinity of $10^{-4}$M or less, $10^{-2}$M or less, $10^{-9}$M or less or with subnanomolar affinity (0.9, 0.8, 0.7, 0.6, 0.5, 0.4, 0.3, 0.2, 0.1 nM or even less). In some embodiments the binding affinity of the antibodies for APCDD1 is at least $1\times10^5$ Ka. In some embodiments the binding affinity of the antibodies for APCDD1 is at least $5\times10^6$ Ka, at least $1\times10^7$ Ka, at least $2\times10^7$ Ka, at least $1\times10^8$ Ka, or greater. Antibodies of the present invention may also be described or specified in terms of their binding affinity to a polypeptide of the invention. In some embodiments binding affinities include those with a $K_d$ less than $5\times10^{-2}$ M, $10^{-2}$ M, $5\times10^{-3}$M, $10^{-3}$ M, $5\times10^{-4}$M, $10^{-4}$ M, $5\times10^{-5}$ M, $10^{-5}$ M, $5\times10^{-6}$ M, $10^{-7}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-1}$ M, $5\times10^{-12}$ M, $10^{-12}$M, $5\times10^{-13}$ M, $10^{-13}$ M, $5\times10^{-14}$ M, $10^{-14}$ M, $5\times10^{-15}$ M, or $10^{-15}$ M, or less.

In some embodiments, the antibodies of the present invention do not bind to known related polypeptide molecules, for example, if they bind APCDD1 polypeptide but not known related polypeptides using a standard Western blot analysis (Ausubel et al, Current Protocols in Molecular Biology, 1994).

In some embodiments, the antibodies of the present invention bind to orthologs, homologs, paralogs or variants, or combinations and subcombinations thereof, of APCDD1. In some embodiments, the antibodies of the present invention bind to orthologs of APCDD1. In some embodiments, the antibodies of the present invention bind to homologs of APCDD1. In some embodiments, the antibodies of the present invention bind to paralogs of APCDD1. In some embodiments, the antibodies of the present invention bind to variants of APCDD1. In some embodiments, the antibodies of the present invention do not bind to orthologs, homologs, paralogs or variants, or combinations and subcombinations thereof, of APCDD1.

In some embodiments, antibodies may be screened against known related polypeptides to isolate an antibody population that specifically binds to APCDD1 polypeptides. For example, antibodies specific to human APCDD1 polypeptides will flow through a column comprising APCDD1-related proteins (with the exception of APCDD1) adhered to insoluble matrix under appropriate buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current Protocols in Immunology, Cooligan at al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff at al., Adv. in Immunol. 43: 1-98, 1988; Monoclonal Antibodies: Principles and Practice, Goding, J. W. (eds.), Academic Press Ltd., 1996; Benjamin at al., Ann. Rev. Immunol. 2: 67-101, 1984). Representative examples of such assays include: concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

The invention also provides antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

In some embodiments the antibodies of the present invention are neutralizing antibodies. In some embodiments the antibodies are targeting antibodies. In some embodiments, the antibodies are internalized upon binding a target. In some embodiments the antibodies do not become internalized upon binding a target and instead remain on the surface.

In some embodiments, the neutralizing antibody will not have any effector functions. Alternatively, a neutralizing antibody can have effector functions.

The antibodies of the present invention can be screened for the ability to either be rapidly internalized upon binding to the tumor-cell antigen in question, or for the ability to remain on the cell surface following binding. In some embodiments, for example in the construction of some types of immunoconjugates, the ability of an antibody to be internalized may be desired if internalization is required to release the toxin moiety. Alternatively, if the antibody is being used to promote ADCC or CDC, it may be mom desirable for the antibody to remain on the cell surface. A screening method can be used to differentiate these types of behaviors. For example, a tumor cell antigen bearing cell may be used where the cells are incubated with human IgG1 (control antibody) or one of the antibodies of the invention at a concentration of approximately 1 μg/mL on ice (with 0.1% sodium azide to block internalization) or 37° C. (without sodium azide) for 3 hours. The cells are then washed with cold staining buffer (PBS+1% BSA+0.1% sodium azide), and are stained with goat anti-human IgG-FITC for 30 minutes on ice. Geometric mean fluorescent intensity (MFI) is recorded by FACS Calibur. If no difference in MFI is observed between cells incubated with the antibody of the invention on ice in the presence of sodium azide and cells observed at 37° C. in the absence of sodium azide, the antibody will be suspected to be one that remains bound to the cell surface, rather than being internalized. If however, a decrease in surface stainable antibody is found when the cells are incubated at 37° C. in the absence of sodium azide, the antibody will be suspected to be one which is capable of internalization.

Antibody Conjugates

In some embodiments, the antibodies of the invention are conjugated. In some embodiments, the conjugated antibodies are useful for cancer therapeutics, cancer diagnosis, or imaging of cancerous cells.

For diagnostic applications, the antibody typically will be labeled with a detectable moiety. Numerous labels are available which can be generally grouped into the following categories:

(a) Radionuclides such as those discussed infra. The antibody can be labeled, for example, with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

The antibodies may also be used for in vivo diagnostic assays. In some embodiments, the antibody is labeled with a radionuclide so that the tumor can be localized using immunoscintiography. As a matter of convenience, the antibodies of the present invention can be provided in a kit, i.e., a packaged combination of reagents in predetermined amounts with instructions for performing the diagnostic assay. Where the antibody is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In some embodiments, antibodies are conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. Cancer Research 52: 127-131. (1992)) to generate a maytansinoid-antibody immunoconjugate. In some embodiments, the conjugate may be the highly potent maytansine derivative DM1 (N2'-deacetyl-N2'-(3-mercapto-1-oxopropyl)-maytansine) (see for example WO02/098883 published Dec. 12, 2002) which has an 1050 of approximately 10-11 M (review, see Payne (2003) Cancer Cell 3:207-212) or DM4 (N2'-deacetyl-N2'(4-methyl-4-mercapto-1-oxopentyl)-maytansine) (see, for example, WO2004/103272 published Dec. 2, 2004).

In some embodiments the antibody conjugate comprises an anti-tumor cell antigen antibody conjugated to one or more calicheamicin molecules. The calicheamicin family of antibiotics is capable of producing double-stranded DNA breaks at sub-picomolar concentrations. Structural analogues of calicheamicin which may be used include, but are not limited to, gamma1I, alpha2I, alpha3I, N-acetyl-gamma1I PSAG and theta1I (Hinman et al. Cancer Research 53: 3336-3342 (1993) and Lode et al. Cancer Research 58: 2925-2928 (1998)). See, also, U.S. Pat. Nos. 5,714,586; 5,712,374; 5,264,586; and 5,773,001, each of which is expressly incorporated herein by reference.

In some embodiments the antibody is conjugated to a prodrug capable of being released in its active form by enzymes overproduced in many cancers. For example, antibody conjugates can be made with a prodrug form of doxorubicin wherein the active component is released from the conjugate by plasmin. Plasmin is known to be over produced in many cancerous tissues (see Decy et al, (2004) FASEB Journal 18(3): 565-567).

In some embodiments the antibodies are conjugated to enzymatically active toxins and fragments thereof. In some embodiments the toxins include, without limitation, diphtheria A chain, nonbinding active fragments of diphtheria toxin, exotoxin A chain (from *Pseudomonas aeruginosa*), *Pseudomonas* endotoxin, ricin A chain, abrin A chain, modeccin A chain, alpha-sarcin, *Aleurites fordii* proteins, dianthin proteins, *Phytolaca americana* proteins (DAPI, and PAP-S), Ribonuclease (RNase), Deoxyribonuclease (Dnase), pokeweed antiviral protein, *momordica charantia* inhibitor, curcin, crotin, sapaonaria officinalis inhibitor, gelonin, mitogellin, restrictocin, phenomycin, neomycin and the tricothecenes. See, for example, WO 93/21232 published Oct. 28, 1993. In some embodiments the toxins have low intrinsic immunogenicity and a mechanism of action (e.g. a cytotoxic mechanism versus a cytostatic mechanism) that reduces the opportunity for the cancerous cells to become resistant to the toxin.

In some embodiments conjugates are made between the antibodies of the invention and immunomodulators. For example, in some embodiments immunostimulatory oligonucleotides can be used. These molecules are potent immunogens that can elicit antigen-specific antibody responses (see Datta et al, (2003) Ann N.Y. Acad. Sci. 1002: 105-111). Additional immunomodulatory compounds can include stem cell growth factor such as "S1 factor", lymphotoxins such as tumor necrosis factor (TNF), hematopoietic factor such as an interleukin, colony stimulating factor (CSF) such as granulocyte-colony stimulating factor (G-CSF) or granulocyte macrophage-stimulating factor (GM-CSF), interferon (IFN) such as interferon alpha, beta or gamma, erythropoietin, and thrombopoietin.

In some embodiments radioconjugated antibodies are provided. In some embodiments such antibodies can be made using $^{32}P$, $^{33}P$, $^{47}Sc$, $^{59}Fe$, $^{64}Cu$, $^{67}Cu$, $^{75}Se$, $^{77}As$, $^{89}Sr$, $^{90}Y$, $^{99}Mo$, $^{105}Rh$, $^{109}Pd$, $^{125}I$, $^{131}I$, $^{142}Pr$, $^{143}Pr$, $^{149}Pm$, $^{153}Sm$, $^{161}Th$, $^{166}Ho$, $^{169}Er$, $^{77}Lu$, $^{186}Re$, $^{188}Re$, $^{189}Re$, $^{194}Ir$, $^{198}Au$, $^{199}Au$, $^{211}Pb$, $^{212}Pb$, $^{213}Bi$, $^{58}Co$, $^{67}Ga$, $^{80m}Br$, $^{99m}Tc$, $^{103m}Rh$, $^{109}Pt$, $^{161}Ho$, $^{189m}Os$, $^{192}Ir$, $^{152}Dy$, $^{211}At$, $^{212}Bi$, $^{223}Ra$, $^{219}Rn$, $^{216}Po$, $^{211}Bi$, $^{225}Ac$, $^{221}Fr$, $^{217}At$, $^{213}Bi$, $^{255}Fm$ and combinations and subcombinations thereof. In some embodiments, boron, gadolinium or uranium atoms are conjugated to the antibodies. In some embodiments the boron atom is $^{10}B$, the gadolinium atom is $^{157}Gd$, and the uranium atom is $^{235}U$.

In some embodiments the radionuclide conjugate has a radionuclide with an energy between 20 and 10,000 keV. The radionuclide can be an Auger emitter, with an energy of less than 1000 keV, a P emitter with an energy between 20 and 5000 keV, or an alpha or 'a' emitter with an energy between 2000 and 10,000 keV.

In some embodiments diagnostic radioconjugates are provided which comprise a radionuclide that is a gamma-, beta-, or positron-emitting isotope. In some embodiments the radionuclide has an energy between 20 and 10,000 keV. In some embodiments the radionuclide is selected from the group of $^{18}F$, $^{51}Mn$, $^{52m}Mn$, $^{52}Fe$, $^{55}Co$, $^{62}Cu$, $^{64}Cu$, $^{68}Ga$, $^{72}As$, $^{75}Br$, $^{76}Br$, $^{82m}Rb$, $^{83}Sr$, $^{89}Zr$, $^{94m}Tc$, $^{51}Cr$, $^{57}Co$, $^{58}Co$, $^{59}Fe$, $^{67}Ga$, $^{75}Se$, $^{97}Ru$, $^{99m}Tc$, $^{114m}In$, $^{123}I$, $^{125}I$, $^{13}Li$ and $^{197}Hg$.

In some embodiments the antibodies of the invention are conjugated to diagnostic agents that are photoactive or contrast agents. Photoactive compounds can comprise compounds such as chromagens or dyes. Contrast agents may be, for example a paramagnetic ion, wherein the ion comprises a metal selected from the group of chromium (III), manganese (II), iron (III), iron (II), cobalt (II), nickel (II), copper (II), neodymium (III), samarium (III), ytterbium (III), gadolinium (II), vanadium (II), terbium (III), dysprosium (III), holmium (III) and erbium(III). The contrast agent may also be a radio-opaque compound used in X-ray techniques or computed tomography, such as an iodine, iridium, barium, gallium and thallium compound. Radio-opaque compounds may be selected from the group of barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. In some embodiments, the diagnostic immunoconjugates may contain ultrasound-enhancing agents such as a gas filled liposome that is conjugated to an antibody of the invention. Diagnostic immunoconjugates may be used for a variety of procedures including, but not limited to, intraoperative, endoscopic or intravascular methods of tumor or cancer diagnosis and detection.

In some embodiments antibody conjugates are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used Agents may be additionally be linked to the antibodies of the invention through a carbohydrate moiety.

In some embodiments fusion proteins comprising the antibodies of the invention and cytotoxic agents may be made, e.g. by recombinant techniques or peptide synthesis. In some embodiments such immunoconjugates comprising the antitumor antigen antibody conjugated with a cytotoxic agent are administered to the patient. In some embodiments the immunoconjugate and/or tumor cell antigen protein to which it is bound is/are internalized by the cell, resulting in increased therapeutic efficacy of the immunoconjugate in killing the cancer cell to which it binds. In some embodiments, the cytotoxic agent targets or interferes with nucleic acid in the cancer cell Examples of such cytotoxic agents include maytansinoids, calicheamicins, ribonucleases and DNA endonucleases.

In some embodiments the antibodies are conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

In some embodiments the antibodies are conjugated to a cytotoxic molecule which is released inside a target cell lysozome. For example, the drug monomethyl auristatin E (MMAE) can be conjugated via a valine-citrulline linkage which will be cleaved by the proteolytic lysozomal enzyme cathepsin B following internalization of the antibody conjugate (see for example WO03/026577 published Apr. 3, 2003). In some embodiments, the MMAE can be attached to the antibody using an acid-labile linker containing a hydrazone functionality as the cleavable moiety (see for example WO02/088172 published Nov. 11, 2002).

Antibody Dependent Enzyme Mediated Prodrug Therapy (ADEPT)

In some embodiments the antibodies of the present invention may be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

In some embodiments the enzyme component of the immunoconjugate useful for ADEPT includes any enzyme capable of acting on a prodrug in such a way so as to convert it into its more active; cytotoxic form.

Enzymes that are useful in ADEPT include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. In some embodiments antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

In some embodiments the ADEPT enzymes are covalently bound to the antibodies by techniques well known in the art such as the use of the heterobifunctional crosslinking reagents discussed above. In some embodiments, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

In some embodiments identification of an antibody that acts in a cytostatic manner rather than a cytotoxic manner can be accomplished by measuring viability of a treated target cell culture in comparison with a non-treated control culture. Viability can be detected using methods known in the art such as the CellTiter-Blue® Cell Viability Assay or the CellTiter-Glo® luminescent Cell Viability Assay (Promega, catalog numbers G8080 and G5750 respectively). In some embodiments an antibody is considered potentially cytostatic if treatment causes a decrease in cell number in comparison to the control culture without any evidence of cell death as measured by the means described above.

In some embodiments an in vitro screening assay can be performed to identify an antibody that promotes ADCC using assays known in the art. One exemplary assay is the In Vitro ADCC Assay. To prepare chromium 51-labeled target cells, tumor cell lines are grown in tissue culture plates and harvested using sterile 10 mM EDTA in PBS. The detached cells are washed twice with cell culture medium. Cells ($5 \times 10^6$) are labeled with 200 μCi of chromium 51 (New England Nuclear/DuPont) at 37° C. for one hour with occasional mixing. Labeled cells are washed three times with cell culture medium, then are resuspended to a concentration of $1 \times 10^5$ cells/mL. Cells are used either without opsonization, or are opsonized prior to the assay by incubation with test antibody at 100 ng/mL and 1.25 ng/mL in PBMC assay or 20 ng/mL and 1 ng/mL in NK assay. Peripheral blood mononuclear cells are prepared by collecting blood on heparin from normal healthy donors and diluted with an equal volume of phosphate buffered saline (PBS). The blood is then layered over LYMPHOCYTE SEPARATION MEDIUM® (LSM: Organon Teknika) and centrifuged according to the manufacturer's instructions. Mononuclear cells are collected from the LSM-plasma interface and are washed three times with PBS. Effector cells are suspended in cell culture medium to a final concentration of $1 \times 10^7$ cells/mL. After purification through LSM, natural killer (NK) cells are isolated from PBMCs by negative selection using an NK cell isolation kit and a magnetic column (Miltenyi Biotech) according to the manufacturer's instructions. Isolated NK cells are collected, washed and resuspended in cell culture medium to a concentration of $2 \times 10^6$ cells/mL. The identity of the NK cells is confirmed by flow cytometric analysis. Varying effector:target ratios are prepared by serially diluting the effector (either PBMC or NK) cells two-fold along the rows of a microliter plate (100 μL final volume) in cell culture medium. The concentration of effector cells ranges from $1.0 \times 10^7$/mL to $2.0 \times 10^4$/mL for PBMC and from $2.0 \times 10^6$/mL to $3.9 \times 10^3$/mL for NK. After titration of effector cells, 100 μL of chromium 51-labeled target cells (opsonized or nonoponsonized) at $1 \times 10^5$ cells/mL are added to each well of the plate. This results in an initial effector:target ratio of 100:1 for PBMC and 20:1 for NK cells. All assays are run in duplicate, and each plate contains controls for both spontaneous lysis (no effector cells) and total lysis (target cells plus 100 μL 1% sodium dodecyl sulfate, 1 N sodium hydroxide). The plates are incubated at 37° C. for 18 hours, after which the cell culture supernatants are harvested tiling a supernatant collection system (Skatron Instrument, Inc.) and counted in a Minaxi auto-gamma 5000 series gamma counter (Packard) for one minute. Results are then expressed as percent cytotoxicity using the formula: % Cytotoxicity=(sample cpm-spontaneous lysis)/(total lysis-spontaneous lysis)×100.

To identify an antibody that promotes CDC, the skilled artisan may perform an assay known in the art. One exemplary assay is the In Vitro CDC assay. In vitro, CDC activity can be measured by incubating tumor cell antigen expressing cells with human (or alternate source) complement-containing serum in the absence or presence of different concentrations of test antibody. Cytotoxicity is then measured by quantifying live cells using ALAMAR BLUE® (Gazzano-Santoro et al., J. Immunol. Methods 202 163-171 (1997)). Control assays are performed without antibody, and with antibody, but using heat inactivated serum and/or using cells which do not express the tumor cell antigen in question. Alternatively, red blood cells can be coated with tumor antigen or peptides derived from tumor antigen, and then CDC may be assayed by observing red cell lysis (see for example Karjalainen and Mantyjarvi, Acta Pathol Microbiol Scand [C]. 1981 October; 89(5):315-9).

To select for antibodies that induce cell death, loss of membrane integrity as indicated by, e.g., PI, trypan blue or 7AAD uptake may be assessed relative to control. One exemplary assay is the PI uptake assay using tumor antigen expressing cells. According to this assay, tumor cell antigen expressing cells are cultured in Dulbecco's Modified Eagle Medium (D-MEM):Ham's F-12 (50:50) supplemented with 10% heat-inactivated FBS (Hyclone) and 2 mM L-glutamine. (Thus, the assay is performed in the absence of complement and immune effector cells). The tumor cells are seeded at a density of $3\times10^6$ per dish in 100×20 mm dishes and allowed to attach overnight. The medium is then removed and replaced with fresh medium alone or medium containing 10 µg/mL of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 mL ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 mL per tube, 3 tubes per treatment group) for removal of cell clumps. Tubes then receive PI (10 mg/mL). Samples may be analyzed using a FACSCAN™ flow cytometer and FACSCONVERT™. CellQuest software (Becton Dickinson). Those antibodies that induce statistically significant levels of cell death as determined by PI uptake may be selected as cell death-inducing antibodies.

Antibodies can also be screened in vivo for apoptotic activity using $^{18}$F-ammexin as a PET imaging agent. In this procedure, Annexin V is radiolabeled with $^{18}$F and given to the test animal following dosage with the antibody under investigation. One of the earliest events to occur in the apoptotic process is the eversion of phosphatidylserine from the inner side of the cell membrane to the outer cell surface, where it is accessible to annexin. The animals are then subjected to PET imaging (see Yagle et al, J Nucl Med. 2005 April; 46(4):658-66). Animals can also be sacrificed and individual organs or tumors removed and analyzed for apoptotic markers following standard protocols.

While in some embodiments cancer may be characterized by overexpression of a gene expression product, the present application further provides methods for treating cancer which is not considered to be a tumor antigen-overexpressing cancer. To determine tumor antigen expression in the cancer, various diagnostic/prognostic assays are available. In some embodiments, gene expression product overexpression can be analyzed by IHC. Paraffin embedded tissue sections from a tumor biopsy may be subjected to the IHC assay and accorded a tumor antigen protein staining intensity criteria as follows:

Score 0: no staining is observed or membrane staining is observed in less than 10% of tumor cells.

Score 1+: a faint/barely perceptible membrane staining is detected in more than 10% of the tumor cells. The cells are only stained in part of their membrane.

Score 2+: a weak to moderate complete membrane staining is observed in more than 10% of the tumor cells.

Score 3+: a moderate to strong complete membrane staining is observed in more than 10% of the tumor cells.

In some embodiments those tumors with 0 or 1+ scores for tumor antigen overexpression assessment may be characterized as not overexpressing the tumor antigen, whereas those tumors with 2+ or 3+ scores may be characterized as overexpressing the tumor antigen.

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of tumor antigen overexpression in the tumor.

Additionally, antibodies can be chemically modified by covalent conjugation to a polymer to increase their circulating half-life, for example. Each antibody molecule may be attached to one or more (i.e. 1, 2, 3, 4, 5 or more) polymer molecules. Polymer molecules are, in some embodiments, attached to antibodies by linker molecules. The polymer may, in general, be a synthetic or naturally occurring polymer, for example an optionally substituted straight or branched chain polyalkene, polyalkenylene or polyoxyalkylene polymer or a branched or unbranched polysaccharide, e.g., homo- or hetero-polysaccharide. In some embodiments the polymers are polyoxyethylene polyols and polyethylene glycol (PEG). PEG is soluble in water at room temperature and has the general formula: $R(O-CH_2-CH_2)_n O-R$ where R can be hydrogen, or a protective group such as an alkyl or alkanol group. In some embodiments, the protective group has between 1 and 8 carbons. In some embodiments the protective group is methyl. The symbol n is a positive integer, between 1 and 1,000, or 2 and 500. In some embodiments the PEG has an average molecular weight between 1000 and 40,000, between 2000 and 20,000, or between 3,000 and 12,000. In some embodiments, PEG has at least one hydroxy group. In some embodiments the hydroxy is a terminal hydroxy group. In some embodiments it is this hydroxy group which is activated to react with a free amino group on the inhibitor. However, it will be understood that the type and amount of the reactive groups may be varied to achieve a covalently conjugated PEG/antibody of the present invention. Polymers, and methods to attach them to peptides, are shown in U.S. Pat. Nos. 4,766,106; 4,179,337; 4,495,285; and 4,609,546 each of which is hereby incorporated by reference in its entirety.

Safety Studies

The antibodies of the invention can be examined for safety and toxicological characteristics. Guidelines for these types of studies can be found in the document issued by the USDA CBER division, "Points to Consider in the Manufacture and Testing of Monoclonal Antibody Products for Human Use" (Federal Register 1997 volume 62(40):9196:9197) incorporated herein by reference. In general, the candidate antibodies should be screened in preclinical studies using a number of human tissue samples and/or isolated human cell types to assess non-target tissue binding and cross reactivity. Following a satisfactory outcome from these human tissue studies, a panel of tissue samples or isolated cells from a variety of animal species can be screened to identify a suitable species for use in general toxicological studies. If no cross reactive animal species is identified, other types of models may be deemed appropriate. These other models can include studies such as xenograft models, where human tumor cells are implanted into a rodent host, or the use of a surrogate monoclonal antibody which recognizes the corresponding tumor-cell antigen in the animal species chosen for the toxicological studies. It should be appreciated that the data from these types of alternate models will be first approximations and proceeding into higher species should be done with caution.

For a candidate naked antibody, studies looking at simple tolerability can be performed. In these studies the therapeutic index of the candidate molecule can be characterized by observing any dose-dependent pharmacodynamic effects. A broad range of doses should be use (for example from 0.1 mg/kg to 100 mg/kg). Differences between tumor cell antigen number, affinity of the candidate antibody for the cross reactive animal target and differences in cellular response following binding of the antibody should be considered in estimating therapeutic index. Pharmacodynamic and pharmacokinetic studies should also be carried out in an appropriate animal model to help guild initial dose considerations when the candidate antibody is tested in humans.

For candidate immunoconjugates, stability studies of the conjugate must be performed in vivo. Optimally, pharmacodynamic and pharmacokinetic studies should be carried out on the individual components of the immunoconjugate to determine the consequences of any breakdown products from the candidate immunoconjugate. Pharmacodynamic and pharmacokinetic studies should also be carried out as above in an appropriate animal model to help guild initial dose considerations. Additional consideration must be given to safety study design when the drug will be given in combination with pretreatment with naked antibody. Safety studies must be carried out with the naked antibody alone, and studies must be designed with the immunoconjugate keeping in mind that the ultimate doses of immunoconjugate will be lower in this type of treatment regimen.

For radio-immunoconjugates, animal tissue distribution studies should be carried out to determine biodistribution data. In addition, an accounting of metabolic degradation of the total dose of administered radioactivity should be performed with both early and late time points being taken. Radio-immunoconjugates can be tested for stability in vitro using serum or plasma, and methods should be developed to measure the percentages of free radionuclide, radio-immunoconjugate and labeled, non-antibody compounds.

Oligonucleotides

In some embodiments, the APCDD1 modulator is an oligonucleotide. In some embodiments, the APCDD1 modulator is an oligonucleotide comprising a sequence selected from the group consisting of SEQ ID NOS:5-21.

In some embodiments the oligonucleotide is an antisense or RNAi oligonucleotide. In some embodiments the oligonucleotide is complementary to a region, domain, portion, or segment of the APCDD1 gene or gene expression product. In some embodiments, the oligonucleotide comprises from about 5 to about 100 nucleotides, from about 10 to about 50 nucleotides, from about 12 to about 35, and from about 18 to about 25 nucleotides. In some embodiments, the oligonucleotide is at least at least 80%, at least 90%, at least 95%, at least 96%, at least 97%, at least 98%, at least 99%, or 100% homologous to a region, portion, domain, or segment of the APCDD1 gene or gene expression product. In some embodiments there is substantial sequence homology over at least 15, 20, 25, 30, 35, 40, 50, or 100 consecutive nucleotides of the APCDD1 gene or gene expression product. In some embodiments there is substantial sequence homology over the entire length of the APCDD1 gene or gene product. In some embodiments, the oligonucleotide binds under moderate or stringent hybridization conditions to a nucleic acid molecule having a nucleotide sequence of SEQ ID NO:1.

In some embodiments, the APCDD1 modulator is a double stranded RNA (dsRNA) molecule and works via RNAi (RNA interference). In some embodiments, one strand of the dsRNA is at least at least 80%, at least 90%, at least 95%, at least 96%, at least 97%, at least 98%, at least 99%, or 100% homologous to a region, portion, domain, or segment of the APCDD1 gene. In some embodiments there is substantial sequence homology over at least 15, 20, 25, 30, 35, 40, 50, 100, 200, 300, 400, 500, or 1000 consecutive nucleotides of the APCDD1 gene. In some embodiments there is substantial sequence homology over the entire length of the APCDD1 gene.

In some embodiments oligonucleotides of the invention are used in a polymerase chain reaction (PCR). This sequence may be based on (or designed from) a genomic sequence or cDNA sequence and is used to amplify, confirm, or detect the presence of an identical, similar, or complementary DNA or RNA in a particular cell or tissue.

Small Molecules

In some embodiments, the APCDD1 modulator is a small molecule. As used herein, the term "small molecule" refers to an organic or inorganic non-polymer compound that has a molecular weight that is less than about 10 kilodaltons. Examples of small molecules include peptides, oligonucleotides, organic compounds, inorganic compounds, and the like. In some embodiments, the small molecule has a molecular weight that is less than about 9, about 8, about 7, about 6, about 5, about 4, about 3, about 2, about 1 or about 0.5 kilodaltons.

Mimetics

In some embodiments, the APCDD1 modulator is a mimetic. As used herein, the term "mimetic" is used to refer to compounds which mimic the activity of a peptide. Mimetics are non-peptides but may comprise amino acids linked by non-peptide bonds. U.S. Pat. No. 5,637,677, issued on Jun. 10, 1997, and parent applications thereof all of which are incorporated herein by reference, contain detailed guidance on the production of mimetics. Briefly, the three-dimensional structure of the peptides which specifically interact with the three dimensional structure of APCDD1 is duplicated by a molecule that is not a peptide. In some embodiments the APCDD1 mimetic is a mimetic of APCDD1 or a mimetic of a ligand of APCDD1.

Methods of Treating/Preventing Cancer

The present invention provides methods for treating and/or preventing cancer or symptoms of cancer in a subject comprising administering to the subject a therapeutically effective amount of one or more APCDD1 modulators of the present invention. In some embodiments the cancer is a cancer associated with overexpression of APCDD1. In some embodiments, the cancer is colon, prostate, lung, bladder, kidney, breast, uterine, ovarian, or pancreatic cancer. In some embodiments, the cancer is colon or prostate cancer. In some embodiments the cancer is a cancer other than colon cancer. In some embodiments the subject has been diagnosed as having a cancer or as being predisposed to cancer. In some embodiments, the subject has been diagnosed as having a cancer or as being predisposed to a cancer other than colon cancer.

Symptoms of cancer are well-known to those of skill in the art and include, without limitation, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like.

A therapeutically effective amount of the modulating compound can be determined empirically, according to procedures well known to medicinal chemists, and will depend, inter alia, on the age of the patient, severity of the condition, and on the ultimate pharmaceutical formulation desired. Administration of the modulators of the present invention can be carried out, for example, by inhalation or suppository or to mucosal tissue such as by lavage to vaginal, rectal, urethral, buccal and sublingual tissue, orally, topically, intranasally, intraperitoneally, parenterally, intravenously, intralymphatically, intratumorly, intramuscularly, interstitially, intra-arterially, subcutaneously, intraoccularly, intrasynovial, transepithelial, and transdermally. In some embodiments, the inhibitors are administered by lavage, orally or inter-arterially. Other suitable methods of introduction can also include rechargeable or biodegradable devices and slow or sustained release polymeric devices. As discussed above, the therapeutic compositions of this invention can also be administered as part of a combinatorial therapy with other known anti-cancer agents or other known anti-bone disease treatment regimen.

The present invention further provides methods of modulating an APCDD1-related biological activity in a patient. The methods comprise administering to the patient an amount of an APCDD1 modulator effective to modulate one or more APCDD1 biological activities. Suitable assays for measuring APCDD1 biological activities are set forth supra and infra.

The present invention also provides methods of inhibiting cancer cell growth in a patient in need thereof comprising administering a therapeutically effective amount of one or more APCDD1 modulators to the patient Suitable assays for measuring APCDD1-related cell growth are known to those skilled in the art and are set forth supra and infra.

The present invention further provides methods of inhibiting cancer in a patient in need thereof. The methods comprise determining if the patient is a candidate for APCDD1 therapy as described herein and administering a therapeutically effective amount of one or more APCDD1 modulators to the patient if the patient is a candidate for APCDD1 therapy. If the patient is not a candidate for APCDD1 therapy, the patient is treated with conventional cancer treatment.

The present invention further provides methods of inhibiting cancer in a patient diagnosed or suspected of having a cancer. The methods comprise administering a therapeutically effective amount of one or more APCDD1 modulators to the patient.

The present invention also provides methods for inhibiting the interaction of two or more cells in a patient comprising administering a therapeutically effective amount of an APCDD1 modulator to the patient. Suitable assays for measuring APCDD1-related cell interaction are known to those skilled in the art and are set forth supra and infra.

The present invention also provides methods of modulating one or more symptoms of cancer in a patient comprising administering to the patient a therapeutically effective amount of one or more APCDD1 modulators.

The present invention further provides methods for inhibiting cell growth in a patient in need thereof comprising administering to the patient a therapeutically effective amount of an APCDD1 modulator. Suitable assays for measuring cell growth are known to those skilled in the art and are set forth supra and infra.

The present invention also provides methods to prophylactically treat a patient who is predisposed to develop cancer, a cancer metastasis or who has had a metastasis and is therefore susceptible to a relapse or recurrence. The methods are particularly useful in high-risk individuals who, for example, have a family history of cancer or of metastasizing tumors, or show a genetic predisposition for a cancer metastasis. In some embodiments the tumors are APCDD1-related tumors. Additionally, the methods are useful to prevent patients from having recurrences of APCDD1-related tumors who have had APCDD1-related tumors removed by surgical resection or treated with a conventional cancer treatment.

The present invention also provides methods of inhibiting cancer progression and/or causing cancer regression comprising administering to the patient a therapeutically effective amount of an APCDD1 modulator.

In some embodiments, the patient in need of anti-cancer treatment is treated with APCDD1 modulators in conjunction with one or more antibodies directed at targets other than APCDD1. In some embodiments, the one or more antibodies directed at targets other than APCDD1 are selected from the group consisting of the EGF receptor, VEGF, CDK4, CDK6 and HER-2.

In some embodiments, the patient in need of anti-cancer treatment is treated with APCDD1 modulators in conjunction with chemotherapy and/or radiation therapy. For example, following administration of the APCDD1 modulators, the patient may also be treated with a therapeutically effective amount of anti-cancer radiation. In some embodiments chemotherapeutic treatment is provided in combination with APCDD1 modulators. In some embodiments APCDD1 modulators are administered in combination with chemotherapy and radiation therapy.

Methods of treatment comprise administering single or multiple doses of one or more APCDD1 modulators to the patient. In some embodiments the APCDD1 modulators are administered as injectable pharmaceutical compositions that are sterile, pyrogen free and comprise the APCDD1 modulators in combination with a pharmaceutically acceptable carrier or diluent.

In some embodiments, the therapeutic regimens of the present invention are used with conventional treatment regimens for cancer including, without limitation, surgery, radiation therapy, hormone ablation and/or chemotherapy. Administration of the APCDD1 modulators of the present invention may take place prior to, simultaneously with, or after conventional cancer treatment. In some embodiments, two or more different APCDD1 modulators are administered to the patient.

In some embodiments the amount of APCDD1 modulator administered to the patient is effective to inhibit one or more of cell proliferation, cell growth, anchorage-independent growth, tumorigenicity, cell cycle regulation, cancer cell motility, cell adhesion, tumor formation, metastasis, cancer cell survival, and cyclin production, among others.

Methods of Perturbing Downstream Gene Expression

In some embodiments, the present invention provides methods of perturbing one or more genes. In some embodiments the method comprises contacting a cell which overexpresses APCDD1 with an APCDD1 modulator. In some embodiments the expression of one or more genes are perturbed in vivo following administration of a therapeutically effective amount of an APCDD1 modulator in the patient. In some embodiments the APCDD1 modulator reduces expression of one or more genes including, for example, cyclin D1.

Combination Therapy

In some embodiments the invention provides compositions comprising two or more APCDD1 modulators to provide still improved efficacy against cancer. In some embodiments the APCDD1 modulators are monoclonal antibodies. Compositions comprising two or more APCDD1 antibodies may be administered to persons or mammals suffering from, or predisposed to suffer from, cancer. One or more antibodies may also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provide of the invention contemplate the administration of combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects. Useful antibodies can include antibodies that target the EGF receptor, e.g., Cetuximab (Erbitux™), antibodies that target EGFR, e.g., Panitumumab (Vectibix™); antibodies that target VEGF, e.g., Bevacizumab (Avastin™) and antibodies that target Her-2, e.g., trastuzimab (Herceptin™).

A cytotoxic agent refers to a substance that inhibits or prevents the function of cells and/or causes destruction of cells. The term is intended to include radioactive isotopes (e.g., $^{131}I$, $^{125}I$, $^{90}Y$, $^{186}Re$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

In some embodiments, conventional cancer medicaments are administered with the compositions of the present invention. Conventional cancer medicaments include:
 a) cancer chemotherapeutic agents;
 b) additional agents;
 c) prodrugs.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine; thioinosine, thiotepa, tegafur, dolastatins, dolastatin, analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, *Coriolus versicolor* extract, tegafur/uracil, estramustine (estrogen/mechlorethamine).

Additional agents which may be used as therapy for cancer patients include EPO, G-CSF, ganciclovir, antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α& β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Clinical Aspects

In some embodiments, the methods and compositions of the present invention are particularly useful in colon, prostate, or breast cancer and cancer metastases.

Pharmaceutical Compositions

The present invention also provides pharmaceutical compositions comprising one or more of APCDD1 modulators and a pharmaceutically acceptable carrier. In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Methods of Detecting APCDD1

The present invention also provides methods for detecting APCDD1. In some embodiments APCDD1 is present in a patient or in a patient sample. In some embodiments the method comprises administering a composition comprising one or more APCDD1 modulators to the patient and detecting the localization of the imaging agent in the patient. In some embodiments the patient sample comprises cancer cells. In some embodiments the APCDD1 modulator is linked to an imaging agent or is detectably labeled. In some embodiments, the APCDD1 modulator is an APCDD1 antibody conjugated to an imaging agent and is administered to a patient to detect one or more tumors or to determine susceptibility of the patient to APCDD1 therapy. The labeled antibodies will bind to the high density of receptors on cells and thereby accumulate on the tumor cells. Using standard imaging techniques, the site of the tumors can be detected.

The present invention also provides methods of imaging/detecting cells or tumors expressing or overexpressing APCDD1 comprising contacting a composition comprising an APCDD1 modulator to a sample and detecting the presence of the APCDD1 modulator in the sample. In some embodiments the sample is a patient sample. In some embodiments the patient sample comprises cancer cells. In some embodiments the APCDD1 modulator is linked to an imaging agent or is delectably labeled.

The present invention also provides methods for quantifying the amount of APCDD1 present in a patient, cell or sample. The methods comprise administering one or more of antibodies, probes, or small molecules to a patient or sample and detecting the amount of APCDD1 present in the sample. In some embodiments the antibodies, probes, or small molecules are linked to an imaging agent or are detectably labeled. Such information indicates, for example, whether or not a tumor is related to APCDD1, and, therefore, whether specific treatments should be used or avoided. In some embodiments, using standard techniques well known to the art-skilled, samples believed to include tumor cells are obtained and contacted with labeled antibodies, probes, oligonucleotides, and small molecules. After removing any unbound, labeled antibodies, probes, oligonucleotides or small molecules, the quantity of labeled antibodies, peptides, oligonucleotides or mimetics bound to the cell, or the quantity of antibodies, peptides, oligonucleotides or mimetics removed as unbound is determined. The information directly relates to the amount of APCDD1 present.

Imaging can be performed using procedures well known to those of ordinary skill in the art. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as an iron chelate. MRI scanning may employ chelates of gadolinium or manganese. Additionally, positron emission tomography (PET) may be possible using positron emitters of oxygen, nitrogen, iron, carbon, or gallium.

In some embodiments the APCDD1 modulator is an APCDD1 antibody. In some embodiments the modulator is linked to an imaging agent or is detectably labeled. In some embodiments the imaging agent is $^{18}F$, $^{43}K$, $^{52}Fe$, $^{57}Co$, $^{67}Cu$, $^{67}Ga$, $^{77}Br$, $^{87}MSr$, $^{86}Y$, $^{90}Y$, $^{99}MTc$, $^{111}In$, $^{123}I$, $^{127}Cs$, $^{129}Ca$, $^{131}I$, $^{132}I$, $^{197}Hg$, $^{203}Pb$, or $^{206}Bi$.

Methods of detection are well known to those of skill in the art. For example, methods of detecting polynucleotides include, but are not limited to PCR, Northern blotting, Southern blotting, RNA protection, and DNA hybridization (including in situ hybridization). Methods of detecting polypeptides include, but are not limited to, Western blotting, ELISA, enzyme activity assays, slot blotting, peptide mass fingerprinting, electrophoresis, immunochemistry and immunohistochemistry. Other examples of detection methods include, but are not limited to, radioimmunoassay (RIA), chemiluminescence immunoassay, fluoroimmunoassay, time-resolved fluoroimmunoassay (TR-FIA), two color fluorescent microscopy, or immunochromatographic assay (ICA), all well known by those of skill in the art. In some embodiments, polynucleotide expression is detected using PCR methodologies and polypeptide production is detected using ELISA technology.

Methods for Delivering a Cytotoxic Agent or a Diagnostic Agent to a Cell

The present invention also provides methods for delivering a cytotoxic agent or a diagnostic agent to one or more cells that express APCDD1. In some embodiments the methods comprise contacting a cell with an APCDD1 modulator conjugated to a cytotoxic agent or diagnostic agent.

Methods for Determining the Prognosis of a Cancer Patient

The present invention also provides methods for determining the prognosis of a patient with an APCDD1-associated cancer. In some embodiments, the methods comprise detecting the presence or absence of evidence of differential expression of APCDD1 in a patient or patient's sample. In some embodiments, the presence of evidence of differential expression of APCDD1 in the patient or sample relative to a control sample is indicative of cancer prognosis. A control sample can be the average level of APCDD1 found in samples from a population of normal healthy individuals (e.g., a population of humans known to be free of cancer), other cancer patients, or a sample from the same patient but at a time when the patient was known to be free cancer. In some cases, a reference chart can be used to determine whether or not a particular level of APCDD1 in a sample is elevated, or normal. For example, a reference chart can contain the normal range of APCDD1 levels found in clinical samples of individuals free of cancer. Using this reference chart, a level of APCDD1 measured in a sample can be classified as being an elevated level or a normal level. By comparing large groups of patients by their APCDD1 levels and other clinical indices known in the art, a statistical pronouncement can be made on the survival chances of a patient with a particular APCDD1 level.

Methods for Determining Susceptibility to APCDD1 Therapy

The present invention also provides methods for determining the susceptibility of a patient to APCDD1 therapy. The methods comprise detecting the presence or absence of evidence of differential expression of APCDD1 in a patient or patient sample. In some embodiments the presence of evidence of differential expression of APCDD1 in the patient or sample is indicative of a patient who is susceptible to APCDD1 therapy. In some embodiments, the absence of evidence of differential expression of APCDD1 in the patient or patient sample is indicative of a patient who is not a candidate for APCDD1 therapy. In some embodiments, a secondary assay can be performed if APCDD1 expression is unchanged or downregulated in the cancer sample as compared to a control sample. Examples of secondary assays include, but are not limited to, monitoring an APCDD1 downstream markers, e.g., cyclin production, in particular cyclin D1; or monitoring cyclin activity, or cell cycle regulation.

In some embodiments, the methods comprise first identifying patients susceptible to APCDD1 therapy comprising administering to the patient in need thereof a composition comprising an APCDD1 modulator linked to an imaging agent and detecting the presence or absence of evidence of the gene or gene product in the patient. In some embodiments, the methods further comprise administering one or more APCDD1 modulators to the patient if the patient is a candidate for APCDD1 therapy and treating the patient with conventional cancer treatment if the patient is not a candidate for APCDD1 therapy.

In some methods, one or more APCDD1 modulators are administered to the patients alone or in combination with other anti-cancer medicaments when the patient is identified as having a cancer or being susceptible to a cancer.

Methods for Assessing the Progression of Cancer

The invention also provides methods for assessing the progression of cancer in a patient comprising comparing the level of an expression product of APCDD1 in a biological sample at a first time point to a level of the same expression product at a second time point. A change in the level of the expression product at the second time point relative to the first time point is indicative of the progression of the cancer.

Methods for Screening

The present invention also provides methods of screening for anti-cancer agents. The methods comprise contacting a cell expressing APCDD1 with a candidate compound and determining whether an APCDD1-related biological activity is modulated. In some embodiments, inhibition of one or more of cell proliferation, cell growth, anchorage-independent growth, tumorigenicity, cell cycle regulation, cancer cell motility, cell adhesion, tumor formation, metastasis, cancer cell survival, and cyclin production, cancer cell survival, cell signaling activity, tumorigenicity, metastasis, cell-to-cell interactions including interactions between APCDD1 and other cell-membrane proteins, and angiogenesis, among others, is indicative of an anti-cancer agent. In some embodiments, anti-cancer agents identified by the methods of the present invention are administered to patients in need thereof in therapeutic and/or diagnostic methods.

In some embodiments, the invention provides methods of screening for anti-cancer agents, particularly anti-metastatic cancer agents, by, for example, screening putative modulators for an ability to modulate the activity or level of a downstream marker. In some embodiments candidate agents that decrease levels of cyclin D1 are identified as anti-cancer agents.

In some embodiments, the invention provides methods for identifying an APCDD1 modulator. In some embodiments the methods comprise comparing phosphorylation of APCDD1 in a sample comprising one or more cells expressing APCDD1 in the presence and absence of a candidate compound. In some embodiments modulation of phosphorylation of APCDD1 in the sample in the presence of the candidate compound as compared to phosphorylation of APCDD1 in the sample in the absence of the candidate compound indicates that the candidate compound is an APCDD1 modulator.

In some embodiments APCDD1 is isolated from the sample using an immunoprecipitating antibody. In some embodiments the immunoprecipitating antibody is an anti-APCDD1 antibody of the present invention.

Methods for Detecting Modulation of APCDD1

In some embodiments, the invention provides methods of detecting modulation of APCDD1 activity in cells. In some embodiments the methods comprise contacting a sample comprising cells which express APCDD1 with an APCDD1 inhibitor for a time sufficient to modulate APCDD1 activity, immunoprecipitating APCDD1 with an APCDD1 antibody of the present invention; and comparing the levels of APCDD1 in the sample with those in a control sample that has not been treated with the APCDD1 inhibitor. In some embodiments alteration of levels of APCDD1 in cells of the sample compared to a control is an indication of the modulation of APCDD1 activity.

In some embodiments, the invention provides methods of detecting modulation of APCDD1 activity in a sample comprising cells which overexpress APCDD1. In some embodiments, the methods comprise overexpressing APCDD1 in the cells for a time sufficient to modulate APCDD1 activity, immunoprecipitating APCDD1 with an APCDD1 antibody of the present invention, and comparing the levels of APCDD1 in the sample with those in a control sample that has not been treated with the APCDD1 inhibitor.

Methods for Purifying APCDD1

In some embodiments, the invention provides methods of purifying APCDD1 protein from a sample comprising APCDD1. The methods comprise providing an affinity matrix comprising an APCDD1 antibody of the present invention bound to a solid support, contacting the sample with the affinity matrix to form an affinity matrix-APCDD1 protein complex, separating the affinity matrix-APCDD1 protein complex from the remainder of the sample; and releasing APCDD1 protein from the affinity matrix.

Kits

In some embodiments, the present invention provides kits for imaging and/or detecting a gene or gene product correlated with differential expression of APCDD1. Kits of the invention comprise detectable antibodies, small molecules, oligonucleotides, decoys, mimetics or probes as well as instructions for performing the methods of the invention. Optionally, kits may also contain one or more of the following: controls (positive and/or negative), containers for controls, photographs or depictions of representative examples of positive and/or negative results.

Each of the patents, patent applications, accession numbers and publications described herein is hereby incorporated by reference in its entirety.

Various modifications of the invention, in addition to those described herein, will be apparent to those of skill in the art in view of the foregoing description. Such modifications are also intended to fall within the scope of the appended embodiments. The present invention is further demonstrated in the following examples that are for purposes of illustration and are not intended to limit the scope of the present invention.

EXAMPLES

Example 1

APCDD1 Expression is Upregulated in Some Cancer Tissues

APCDD1 expression was analyzed in a panel of normal and cancerous human tissues. Tissues types included heart, liver, adrenal, brain, prostate, kidney, breast, colon, lung and pancreas. Elevated levels of APCDD1 expression relative to both normal tissues and other cancerous tissues were observed in colon cancer (FIG. 1).

APCDD1 expression was further analyzed in samples from primary and metastatic colon cancer samples (FIG. 2). mRNA was isolated from laser capture microdissected (LCM) primary or metastatic colon cancer tissues, and the mRNA was compared to either a pool of respective normal tissue or normal cells adjacent to the cancer cells within each tissue sample. Samples were tested by oligonucleotide array analysis on either Affymetrix® GeneChips® (Affymetrix, Inc., Santa Clara, Calif.) ("Affy") or arrays that were generated in-house using cDNA libraries made from cancerous tissue (EVD). The number of patients' samples analyzed with each array is indicated, followed by the relative differences in expression between the cancer and the normal samples. For example, ">=2X", ">=3X", ">=5X", denote up-regulation by 2-, 3- and 5-fold respectively; "<=2x" denotes down-regulation by 2-fold. Analysis of both sets of gene arrays demonstrated that APCDD1 is up-regulated in colon cancer.

Figure 3:
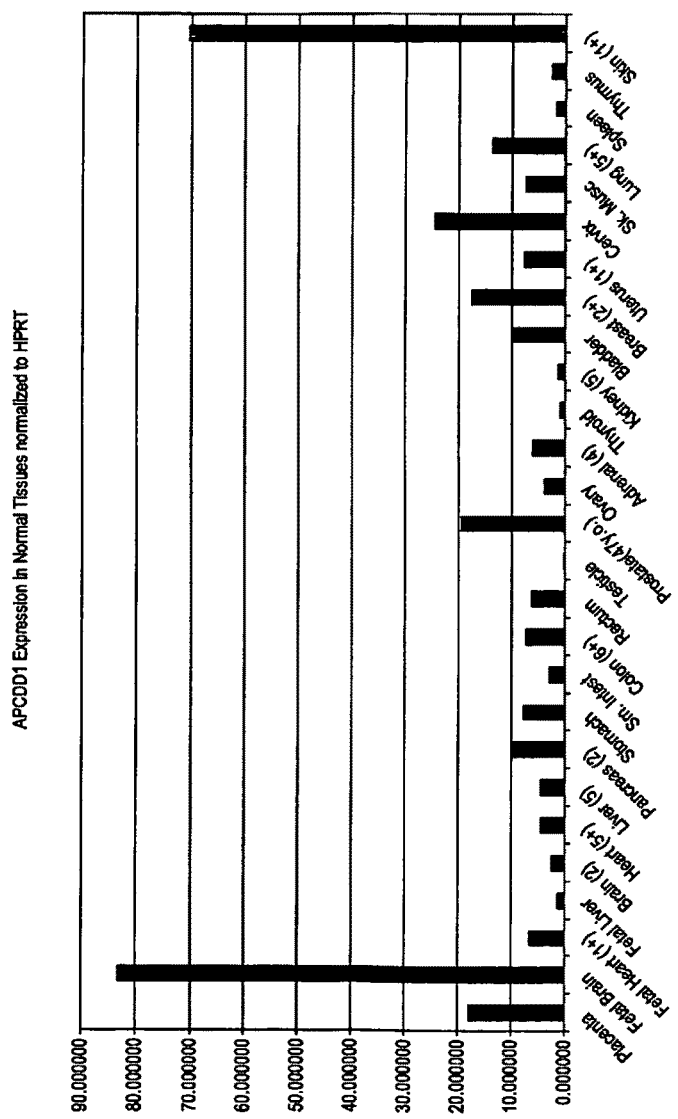
FIG. 3 depicts a graphical representation of APCDD1 mRNA levels in normal tissues. Normal tissue types are described along the x-axis.
Figure 4:
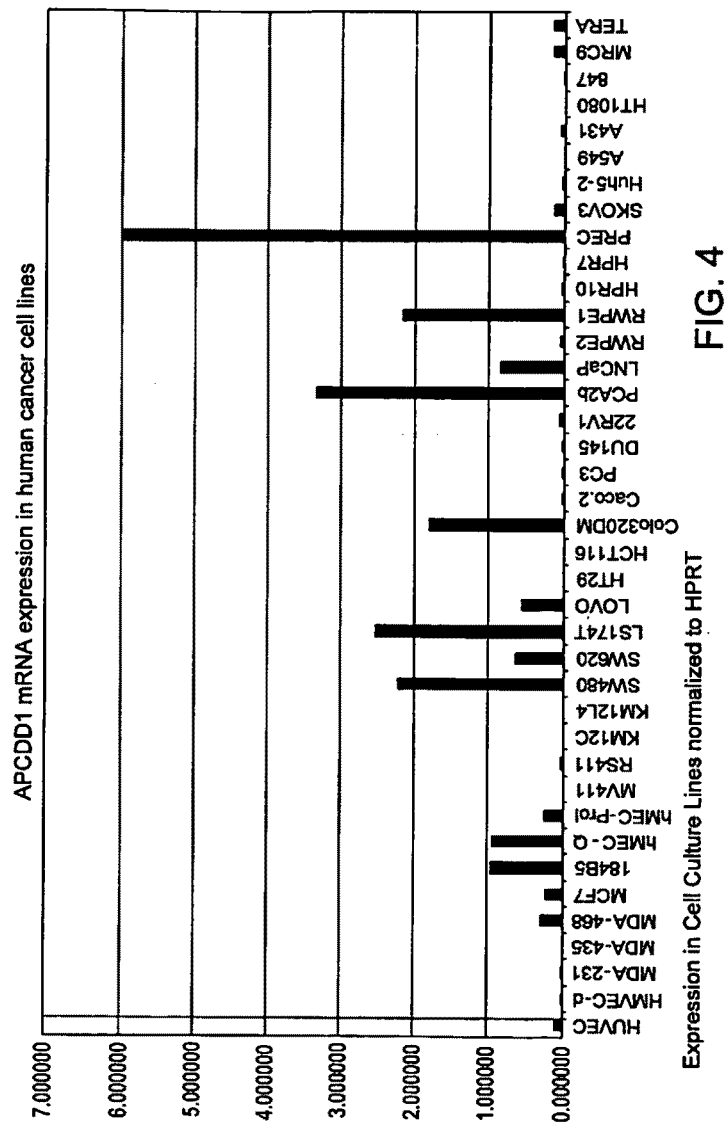
FIG. 4 depicts a graphical representation of APCDD1 mRNA levels in human cancer cell lines.

APCDD1 mRNA levels in a larger panel of 27 normal human tissue types (FIG. 3) and 39 human cell lines (FIG. 4) were analyzed by semi-quantitative RT-PCR (GeneAmp®, Applied Biosystems, Foster City, Calif. The forward primer was: GTCGAGGAGCTCTTCCTTGGTGACATT (SEQ ID NO:24) while the reverse primer was: TGGTGCTCGTCT-GACCGATAGATGAT (SEQ ID NO:25). Among the normal tissues tested, fetal brain, skin, cervix and prostate showed the highest relative expression. Among the cell lines, the highest relative levels of expression were noted in a normal human prostate epithelial cell line (PrEC), a prostate cancer cell line (PCA2b), as well as in a number of human colon cancer cell lines, including LS174T, SW480, SW620 and LoVo.

Example 2

Immunolocalization analysis of APCDD1 Protein in Human Tissues and Cell Lines

APCDD1 protein expression was analyzed by immunohistochemistry in human tissues (placenta) and cell lines (SW620, Colo320, AGS, HCT116, HT29, PREC, PCA2b, PC3, 293T and 293T transformed with APCDD1. Punctate cytoplasmic staining was observed in APCDD1-expressing cell types. Staining was scored according to an intensity scale spanning from 0-3. The results of this experiment are summarized in Tables 1 and 2. IHC experiments were carried out using a rabbit polyclonal antibody raised against the ECD of APCDD1. APCDD1 protein was detected in 293T cells transfected with an APCDD1 expressing construct and not in untransfected cells. This result suggests that the APCDD1 antibody specifically recognizes APCDD1 protein. Staining also indicated that APCDD1 was expressed in colon cancer (SW620 and HCT116), prostate cancer (PC3 and PCA2b) cell lines and also in PREC normal epithelial prostate cell line.

TABLE 1

APCDD1 levels in human tissues and cell lines

|  |  |  | No Prim | Rb IgG | APCCD1 |
|---|---|---|---|---|---|
| A1 | P05-124 | 293T | 0 | 0 | Blush |
| A2 | P05-124 | 293T | 0 | 0 | Blush |
| A3 | P05-282 | 293T + APCDD1 | 0 | 0 | [95%] 3/slt bkgd |
| A4 | P05-282 | 293T + APCDD1 | 0 | 0 | [95%] 3/slt bkgd |
| B1 | P05-1033 | SW620 | 0 | 0 | [10%] 2+; [50%] 1 |
| B2 | P05-1033 | SW620 | 0 | 0 | [10%] 2+; [50%] 1 |
| B3 | P05-1275 | PREC | 0 | Blush | [80%] 1+ |
| B4 | P05-1275 | PREC | 0 | Blush | [80%] 1+ |
| C1 | P05-613 | PCA2b | 0 | Blush | [100%] 2+ |
| C2 | P05-613 | PCA2b | 0 | Blush | [100%] 2+ |
| C3 | P04-1379 | HCT116 | 0 | 0 | [95%] >1 |
| C4 | P04-1379 | HCT116 | 0 | 0 | [95%] >1 |
| D1 | P04-1029 | PC3 | 0 | 0 | [100%] 1+ |

TABLE 1-continued

APCDD1 levels in human tissues and cell lines

|  |  |  | No Prim | Rb IgG | APCCD1 |
|---|---|---|---|---|---|
| D2 | P04-1029 | PC3 | 0 | 0 | [100%] 1+ |
| D3 | 4514-1 | Placenta | 0 | Blush | Trophoblast 2-3+ |

TABLE 2

APCDD1 Levels in human tissues and cell lines

|  |  |  | No Prim | Rb IgG | APCCD1 |
|---|---|---|---|---|---|
| A1 | P05-124 | 293T | 0 | 0 | 0 |
| A2 | P05-124 | 293T | 0 | 0 | 0 |
| A3 | P05-282 | 293T + APCDD1 | 0 | 0 | [75%] 3+ |
| A4 | P05-282 | 293T + APCDD1 | 0 | 0 | [75%] 3+ |
| B1 | P05-1033 | SW620 | 0 | 0 | Rare+ |
| B2 | P05-1033 | SW620 | 0 | 0 | Rare+ |
| B3 | P05-1275 | PREC | 0 | Blush | [25%] 1-2+ |
| B4 | P05-1275 | PREC | 0 | Blush | [25%] 1-2+ |
| C1 | P05-613 | PCA2b | 0 | 0 | [40%] 1-2+ |
| C2 | P05-613 | PCA2b | 0 | 0 | [40%] 1-2 + p |
| C3 | P04-1379 | HCT116 | 0 | 0 | [10%] 1 + p |
| C4 | P04-1379 | HCT116 | 0 | 0 | [10%] 1+ |
| D1 | P04-1029 | PC3 | 0 | 0 | [100%] 1-2+ |
| D2 | P04-1029 | PC3 | 0 | 0 | [100%] 1-2+ |
| D3 | 4514-1 | Placenta | 0 | 0 | 1-2+ |

Figure 5:
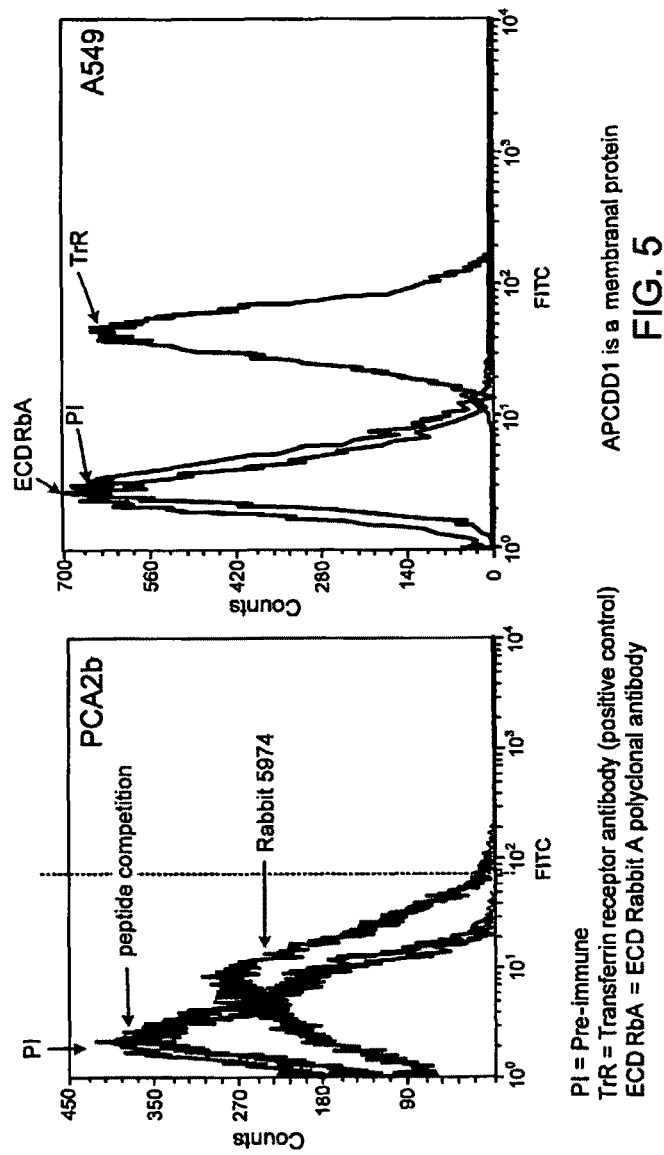
FIG. 5 depicts a FACS analysis of APCDD1 immunolocalization.

APDCC1 was also analyzed by immunohistochemistry. Cell types analyzed were 293T and 293T transformed with APCDD1, SW620, HCT116, PREC, PCA2b, PC3. Tissue sections were deparaffinized and antigen retrieval was performed on a Ventana Discovery instrument (Ventana Medical Systems, Inc., Tucson, Ariz.). Standard cell conditioning was performed, and then cells were incubated for 60 minutes with primary antibodies. A rabbit anti-human APCDD1 antibody (Chiron, Emeryville, Calif.) and rabbit IgG Prebleed control (Chiron, Emeryville, Calif.) were used at 10 µg/ml Ventana Universal Secondary Reagent (Ventana Medical Systems, Inc.) followed by Ventana DAB Map Kit (Ventana Medical Systems, Inc.) was used for detection. Ventana Hematoxylin and Bluing Reagents (Ventana Medical Systems, Inc.) were used for counterstain, and sections were dehydrated in graded alcohols, cleared in xylene and coverslipped using a synthetic mounting media. The IHC analysis indicated that APCDD1 was detectable in 293T cells transformed with APCDD1, as well as in the untransformed cell lines, SW620, PREC, PCA2b. The localization of the APCDD1 protein in the cell membrane was confirmed by FACS analysis (FIG. 5).

Example 3

APCDD1 Protein Expression in Human Cancer Cell Lines

APCDD1 protein expression in human cancer cell lines was probed in a panel of human cancer cell lines that included 293T cells transformed with APCDD1, Colo 205, Colo320dm, HT29, LNCaP, PC3, PCA2b and SW620. Protein lysates were made from cell pellets and the lysates were subjected to immunoprecipitation with an anti-APCDD1 antibody. Proteins captured by immunoprecipitation were separated by acrylamide gel electrophoresis and then subjected to immunoblotting analysis.

Figure 6:
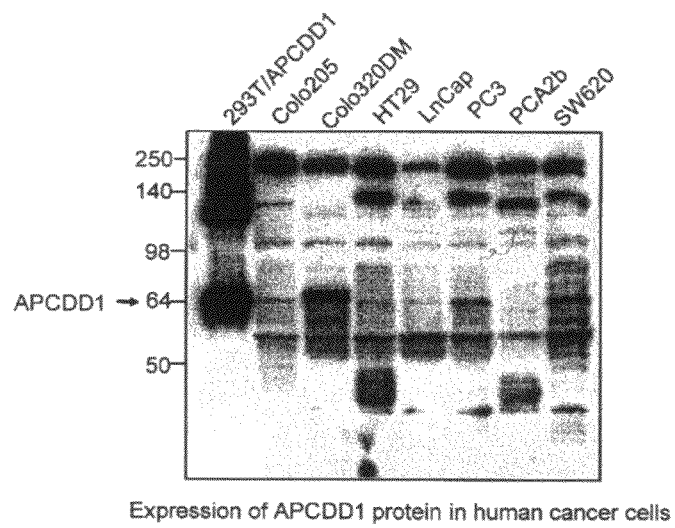
FIG. 6 depicts an immunoprecipitation analysis showing APCDD1 protein isolated from eight different human cell lines.

A polypeptide of about 64 kD was detected in lysates from 293T cells transformed with APCDD1, Colo 205, Colo320dm, HT29, LnCaP, PC3, and SW620 (FIG. 6). The 293/APCDD1 extract also contained a polypeptide of about 58 kD. The relative levels of the APCDD1 immunoprecipitation product varied among the cell lines, with the highest levels observed in 293T cells transformed with APCDD1, Colo320dm and SW620 cells.

Figure 7:
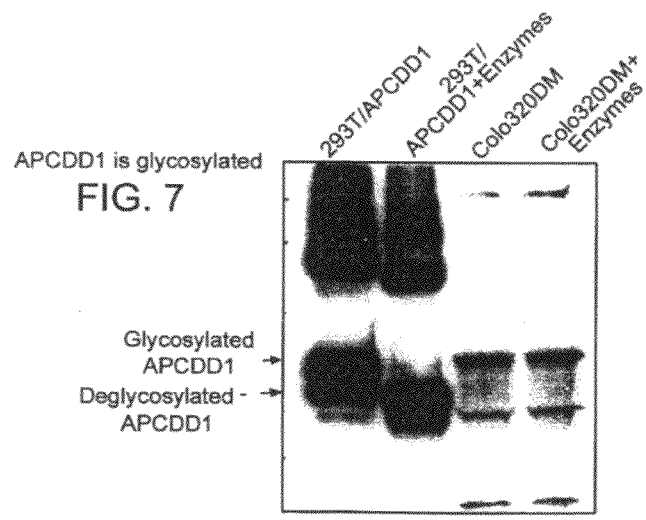
FIG. 7 depicts an immunoprecipitation analysis of the glycosylation status of the APCDD1 protein.

Since the 64 kD polypeptide was slightly larger that the predicted 58.7 kD APCDD1 gene product, the glycosylation status of the polypeptide was evaluated by enzymatic hydrolysis. Enzymatic treatment of extracts from 293 cells transformed with APCDD1 eliminated the 64 kD species and shifted the bulk of the immunoprecipitation products into a more rapidly migrating doublet of about 54-58 kD (FIG. 7), suggesting that the APCDD1 protein is glycosylated. A corresponding shift was not observed in extracts from Colo320dm cells.

Example 4

Functional Assays

The role of APCDD1 in cell proliferation was evaluated in a series of experiments that explored 1) the effects of reducing APCDD1 expression and 2) the effects of overexpressing APCDD1. APCDD1 expression was reduced by siRNA methods. A panel of siRNAs was tested for the ability to reduce APCDD1 mRNA levels in Colo320 cells (a colon cancer cell line expressing APCDD1). The sequences of the siRNAs used in these studies are presented in Table 3.

siRNA analysis was performed as follows. Cells were seeded in 96-well dishes at a density that resulted in about 80-95% confluence after 1 day. Oligonucleotides were diluted to 2 μM in OptiMEM™ (Invitrogen, Carlsbad, Calif.). The oligonucleotide-OptiMEM™ was then added to a delivery vehicle that had been optimized for the particular cell type used in the assay. The oligo/delivery vehicle mixture was then further diluted into medium with serum such that the final concentration in the of siRNA oligonucleotides in the cell culture plates was 50 nM. Cells were incubated at 37° C. in the oligonucleotide/delivery vehicle mixture from about 4 hours to overnight depending upon the cell type. The transfection mixture was then replaced with fresh medium and the cells were cultured for either 48 or 72 hours. Transfected cells were harvested by trypsinization and APCDD1 mRNA levels were assayed by RT-PCR as described in Example 1.

Figure 8:
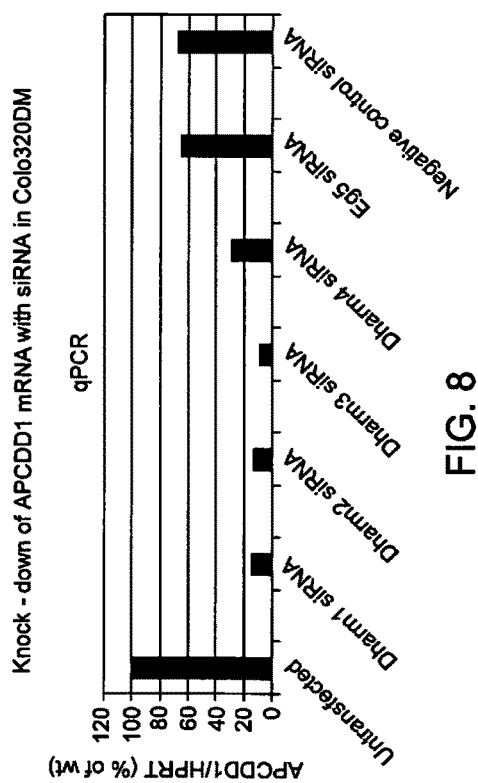
FIG. 8 depicts a graphical representation of APCDD1 mRNA levels in Colo320 cells following administration of siRNAs. The y-axis is a ratio of APCDD1 mRNA relative to that of HPRT mRNA, an internal control RNA. UT=untransfected; Eg5=siRNA targeting Eg5 (an irrelevant gene); Neg Control=an siRNA sequence not homologous with any known gene.
Figure 9:
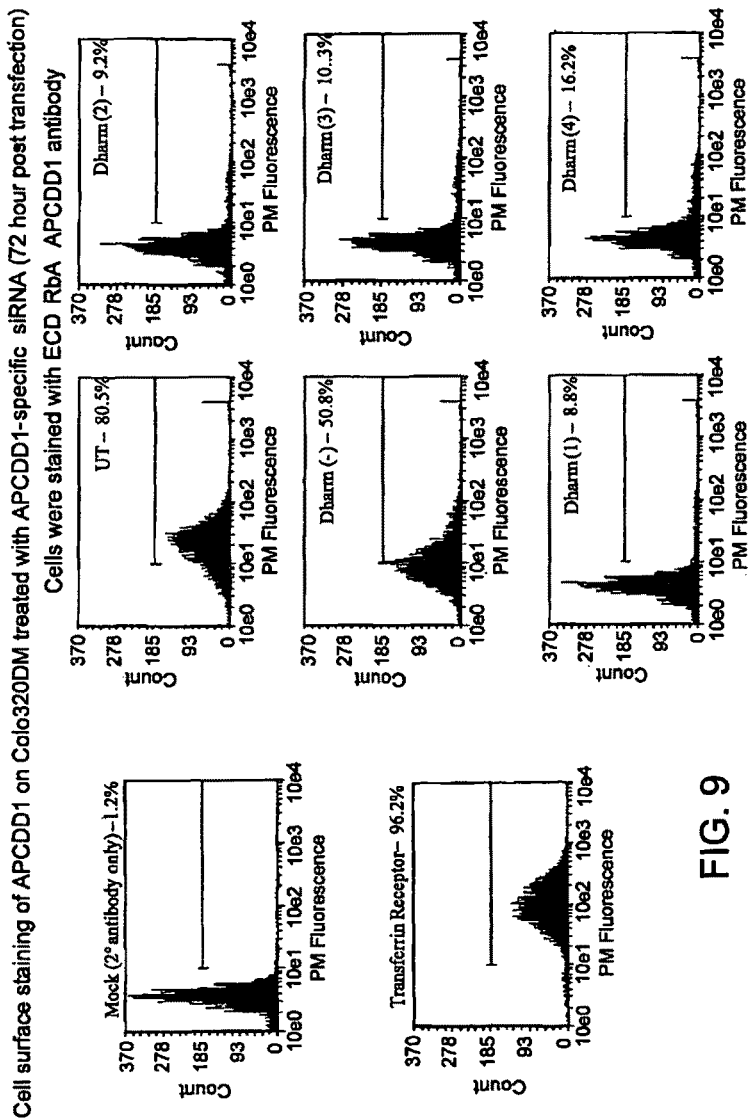
FIG. 9 depicts a FACS analysis of the effect of APCDD1-specific siRNAs on APCDD1 protein levels in Colo 320 cells. The "Pos. Control" is an Eg5 siRNA targeting Eg5. The "Neg. control" is a siRNA sequence not homologous with any known gene. The y-axis measures the luminescence level, which is proportional to the number of dead cells.
Figure 10:
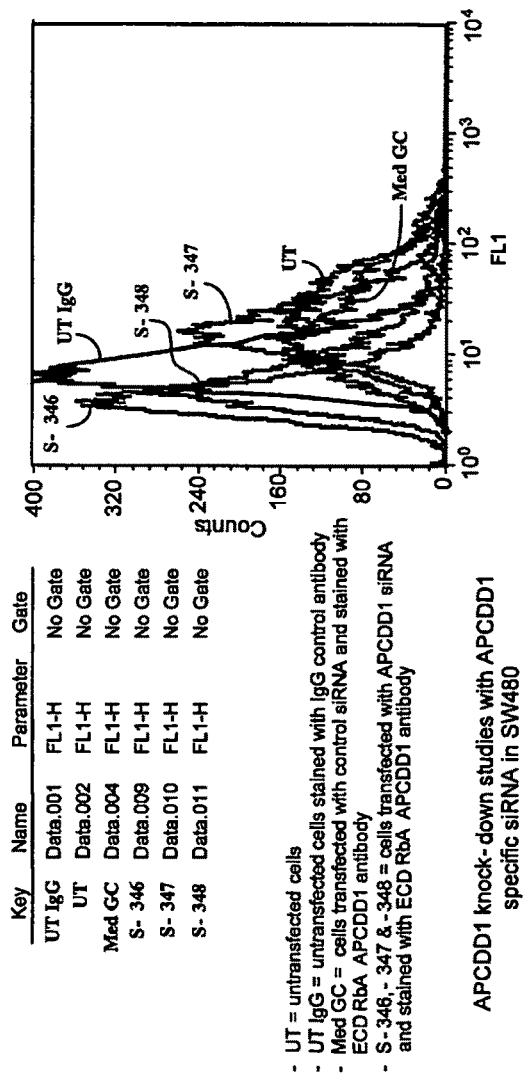
FIG. 10 depicts a FACS analysis of the effect of APCDD1-specific siRNAs on APCDD1 protein levels in SW480 cells.

As shown in FIG. 8, all four APCDD1 siRNAs tested reduced APCDD1 mRNA levels. Similar effects on APCDD1 mRNA were not observed with the non-specific control siRNAs, Eg5 and (−). The reduction in APCDD1 mRNA by the APCDD1 siRNAs also resulted in a reduction of APCDD1 protein expression. FACS analysis of both Colo320 (FIG. 9) and SW480 cells (FIG. 10) that had been transfected with APCDD1 siRNAs indicated a specific reduction in APCDD1 cell surface staining.

APCDD1 siRNAs were then evaluated for their effects on cell proliferation using a panel of cell lines that included Colo 320, SW 620, PC3 and A549 cells. siRNA transfections were performed as above and cell proliferation was measured using a commercially available kit (ToxiLight®, Cambrex Corporation, East Rutherford, N.J.). APCDD1 siRNA-dependent decreases in cell proliferation were noted for all the cell lines tested, although because the magnitude of the decrease varied according to both the specific siRNA that was used and the cell type under consideration, the results of these studies were inconclusive.

Figure 11:
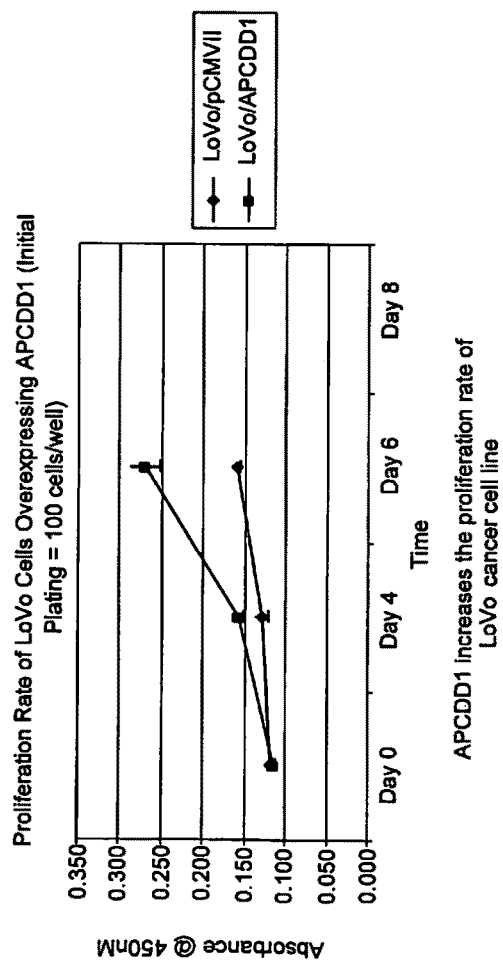
FIG. 11 depicts a graphical representation of the effect of overexpression of APCDD1 on cell proliferation in LoVo cells.

The effect of APCDD1 on cell proliferation was further evaluated in experiments in which the APCDD1 gene product was overexpressed. LoVo cells were transfected with APCDD1 that had been inserted into a pCMVII vector. Control cells were transfected with pCMVII. Cell numbers were measured at 4 and 6 days after transfection. At both timepoints (FIG. 11), the relative cell numbers in the APCDD1 transfected samples was significantly higher than those of the control cells (about 20% greater on day 4 and about 80% greater on day 6).

In another experiment, Rat-1 cells were transfected with an APCDD1-expressing plasmid. The transfected cells were evaluated for their ability to support anchorage-independent growth as assayed by colony formation in soft agar. Soft agar assays were performed by first coating a non-tissue culture treated plate with Poly-HEMA to prevent cells from attaching to the plate. Non-transfected cells were harvested using trypsin and washing twice in media. The cells were counted using a hemacytometer and resuspended to 104 cells per ml in media. Fifty μl aliquots were placed in polyHEMA coated 96-well plates and transfected.

The day after transfection, cells were trypsinized, resuspended and counted. Cells were diluted to about 500 cells/100 μl/well and transferred to a deep well block (max volume=1 ml/well, in triplicate, following standard placement). Cells were plated in two plates: Corning #7007 Ultra Low Adherent U-plate for the assay, and Corning #3799 for the plating efficiency check. Seaplaque GTG Agarose 3% was melted in a microwave oven by heating about 1 minute. When fully melted, about 10 ml was poured into pre-warmed 50 ml polypropylene tubes (Falcon #35-2070) and incubated in the 60° C. heatblock for at least 10 minutes. About 18.6 ml complete media was added to a 50 ml polypropylene tube and incubated at about 37° C. in a water bath. A Multimek™ pipettor was used to dispense agarose to cells in 96 well plates. About 18.6 ml warm media was poured into the 10 ml of agarose and mixed well by gentle inversion. Plates were incubated at about 4° C. for 20-30 min to let the agarose solidify quickly. After agarose was solidified, 100 μl complete media was added over the cells. To measure the Day 0 plating efficiency, about 25 μl/well Alamar Blue was added and incubated overnight at 37° C. Plates were then read after 18-24 hr@530ex/590em on a TECAN plate reader. Assay plates were incubated at 37° C. for 7 days before developing with Alamar Blue (25 μl/well).

Expression levels of Rat-1/APCDD1 clones were evaluated by immunoblotting. Five out of five clones tested did not form colonies in soft agar.

Figure 12:
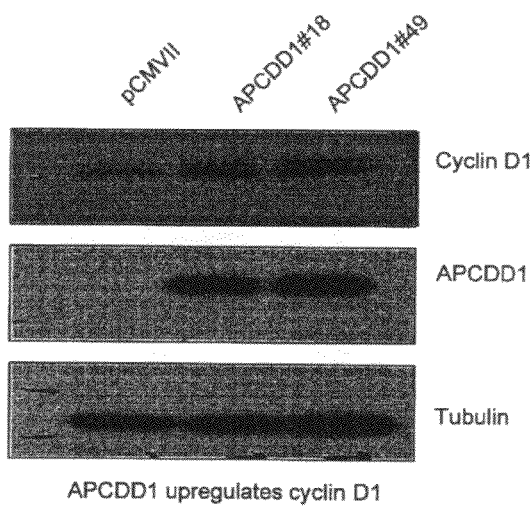
FIG. 12 depicts immunoblots showing the effect of overexpression of APCDD1 on cyclin D1 expression in Rat 1 cells.

The expression of cyclin D1, a key regulator of the cell cycle, was evaluated in RAT-1/APCDD-1 transformants. As shown in FIG. 12, immunoblotting experiments indicated that cyclin D1 levels were elevated in two independent Rat-1/APCDD1 stable cell lines (APCDD1#18 and APCDD1#49) relative to a control cell line that had been transformed with pCMVII vector alone.

Example 5

Sequences

Various APCDD1 sequences are set forth in the appended sequence listing, which is herein incorporated by reference in its entirety. SEQ ID NO:1 represents an APCDD1 mRNA sequence (GenBank Accession No. NM_153000); (CDS 354 . . . 1898).

SEQ ID NO:2 represents an amino acid sequence of APCDD-1 (GenBank Accession No. NM_153000).

SEQ ID NO:3 represents an amino acid sequence of an extracellular domain (ECD) of APCDD1.

SEQ ID NO:4 represents a signal peptide sequence of APCDD1.

Example 6

APCDD1 Antibodies

The characteristics of the anti-APCDD1 antibodies used in these experiments are summarized in Table 3.

TABLE 3

Antibodies targeting the APCDD1 polypeptide

| Source name | APCDD-1 Specificity | Epitope | Species |
|---|---|---|---|
| Chiron ECD SbA D70 | Human | ECD | Rb |
| Chiron ECD RbA D70 | Human | ECD | Rb |
| Chiron B5974 | Human | QRPSDGSSPDRPEKRATSYQ (SEQ ID NO: 23) | Rb |
| Chiron B5635 | Human | PSSYQPPLQNAKNHDH (SEQ ID NO: 22) | Rb |
| Chiron Rat#4 | Human | full length APCDD1 cDNA | Rat monoclonal |

The activity and specificity of the polyclonal anti-APCDD1 antibodies was confirmed in three ways: 1) immunoblotting against extracts from 293T cells transformed with APCDD1; 2) immunobinding and FACS analysis of APCDD1 expressing cell lines, i.e., SW620, SW480, Colo320 and PC2b; and immunoprecipitation of 293T/APCDD1 transformed cell extracts. The validation data for the antibodies are summarized in Table 3.

TABLE 4

Anti-APCDD1 antibody validation data

| | Antibody name | | | | |
|---|---|---|---|---|---|
| Method | ECD RBA D70 | ECD RBA D70 | B5974 | B5635 | Rat#4, monoclonal |
| Immuno-blotting | + | + | + | + | + |
| FACS | +SW620, SW480, Colo320 | ND* | +PC2b | +(peptide did not compete) | +PC2b, Colo 320, SW480 |

TABLE 4-continued

Anti-APCDD1 antibody validation data

| | Antibody name | | | | |
|---|---|---|---|---|---|
| Method | ECD RBA D70 | ECD RBA D70 | B5974 | B5635 | Rat#4, monoclonal |
| Immuno-precipitation | + | ND* | + | + | |

*not determined

Figure 13:
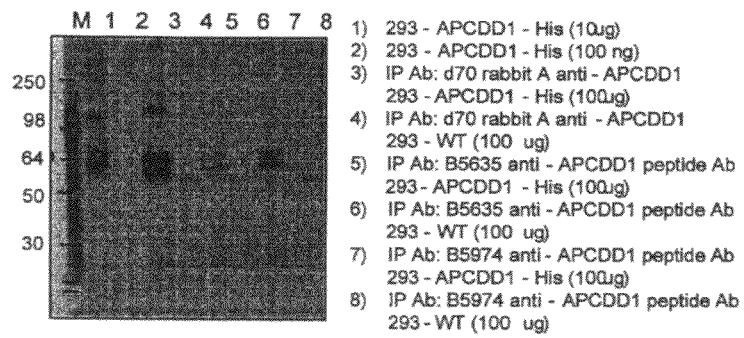
FIG. 13 depicts an immunoprecipitation analysis of a panel of anti-APCDD1 polyclonal antibodies.
Figure 14A:
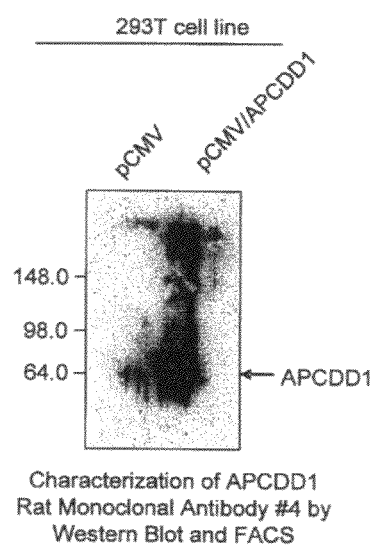
FIG. 14 depicts an immunoblot (FIG. 14A) and FACS (FIG. 14B) analysis of Rat#4 anti-APCDD1 monoclonal antibody.
Figure 14B:
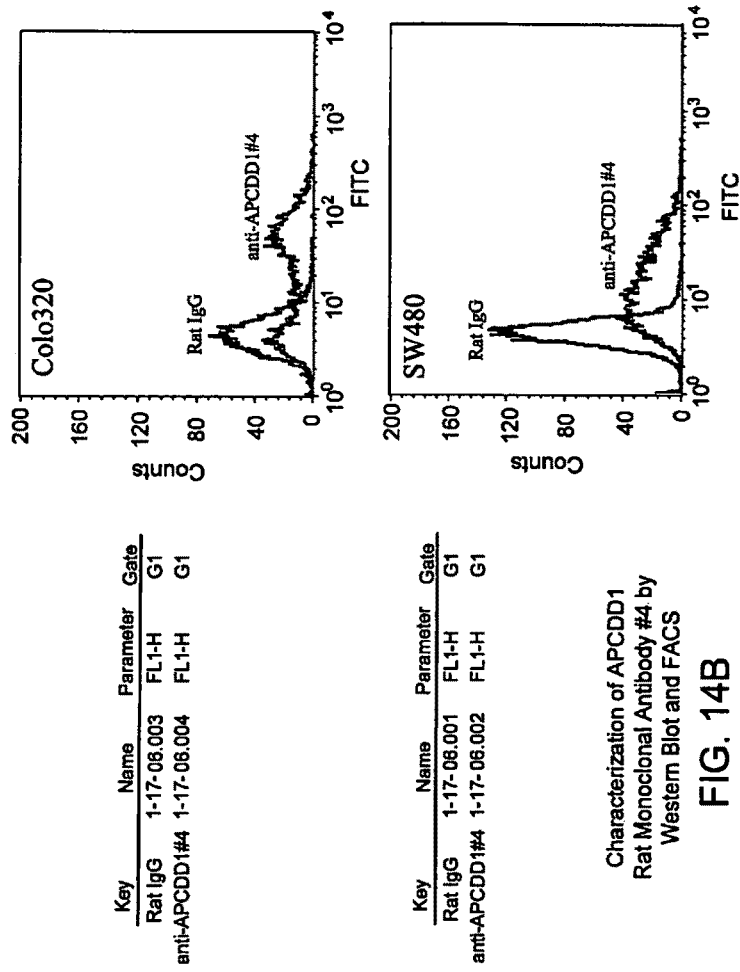

The immunoprecipitation data for the polyclonal antibodies is shown in FIG. 13. Immunoprecipitation was performed according to the method described in Example 3 using Qiagen Penta His antibody, BSA-free (cat. number#34660). The immunoblotting and FACS data for the Rat#4 monoclonal antibody are shown in FIGS. 14A and 14B.

Example 7

APCDD1 siRNAs

Sequences of the siRNAs used in Example 4 are provided in Table 5.

TABLE 5

APCDD1 siRNAs

| Sample Name | | Sequence | SEQ ID NO: |
|---|---|---|---|
| Dharm1 | sense sequence: | GCUCAAACAUCUCCACAAUUU | 5 |
| | antisense sequence: | AUUGUGGAGAUGUUUGACCUU | 6 |
| Dharm2 | sense sequence: | CUUCAAGGCCUACCAAUUUUU | 7 |

TABLE 5-continued

APCDD1 siRNAs

| Sample Name | | Sequence | SEQ ID NO: |
|---|---|---|---|
| | antisense sequence: | AAAUUGGUAGGCCUUGAAGUU | 8 |
| Dharm3 | sense sequence: | CAAACUACCUCACACGGAGUU | 9 |
| | antisense sequence: | CUCCGUGUGAGGUAGUUUGUU | 10 |
| Dharm4 | sense sequence: | GCCCAGAGUUCAUCACAAGUU | 11 |
| | antisense sequence: | CUUGUGAUGAACUCUGGGCUU | 12 |
| APCDD1-1 | sense sequence: | GGUCUCAUCCUAGGUCCUUTT | 13 |
| | antisense sequence: | AAGGACCUAGGAUGAGAACCTG | 14 |
| APCDD1-2 | sense sequence: | GGGCUUUUAAGGAGUCACATT | 15 |
| | antisense sequence: | UGUGACUCCUUAAAAGCCCTC | 16 |
| APCDD1-3 | sense sequence: | GGUGUAGAUAUGUAUAUACTT | 17 |
| | antisense sequence: | GUAUAUACAUAUCUACACCTG | 18 |
| S346 | UCACUUUGAACACGAACUCGG UGCC | | 19 |
| S347 | UUACUUCACAGCCUGUGGAGA CCCA | | 20 |
| S348 | UAAGUGGGAUUUGUGCACCGG UUGC | | 21 |

Example 8

APCDD1 Epitopes

Peptide epitopes of APCDD1 recognized by the antibodies used in Examples 2 and 3 are provided in Table 6.

TABLE 6

Exemplary APCDD1 Epitopes

| Epitope | Amino acids of APCDD-1 (SEQ ID NO: 2) | Domain | SEQ ID NO: |
|---|---|---|---|
| PSSYQPPLQNAKNHDH | 247-262 | Extracellular | 22 |
| QRPSDGSSPDRPEKRATSYQ | 441-460 | Extracellular | 23 |

While the present invention has been described with reference to the specific embodiments thereof it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention.

What is claimed is:

1. A method for detecting a prostate cancer cell in a patient comprising administering to the patient a composition comprising an APCDD1 antibody that binds an epitope in the APCDD1 extracellular domain (ECD) (SEQ ID NO. 2) linked to an imaging agent and detecting the localization of the imaging agent in the patient and one or more pharmaceutically acceptable carriers.

2. The method of claim 1 wherein the APCDD1 antibody binds an epitope in the extracellular domain (ECD) consisting of SEQ ID NO: 22 or SEQ ID NO:23 of APCDD1.

3. The method of claim 1, wherein the imaging agent is $^{18}$F, $^{43}$K $^{52}$Fe, $^{57}$Co, $^{67}$Cu, $^{67}$Ga, $^{77}$Br, $^{87M}$Sr, $^{86}$Y, $^{90}$Y, $^{99M}$Tc, $^{111}$In, $^{112}$I, $^{125}$I, $^{127}$Cs, $^{129}$Cs, $^{131}$I $^{132}$I $^{197}$Hg, $^{203}$Pb, or $^{206}$Bi.

4. The method of claim 1 wherein the imaging agent is an enzyme or fluorophore.

* * * * *